United States Patent
Getautis et al.

(10) Patent No.: US 12,317,741 B2
(45) Date of Patent: May 27, 2025

(54) PHOTOVOLTAIC DEVICES CONTAINING CYCLOBUTANE-BASED HOLE TRANSPORTING MATERIALS

(71) Applicants: Kaunas University of Technology, Kaunas (LT); SWISS FEDERAL INSTITUTE OF TECHNOLOGY LAUSANNE, Lausanne (CH)

(72) Inventors: Vytautas Getautis, Kaunas (LT); Kasparas Rakstys, Kaunas (LT); Maryte Daskeviciene, Jonava (LT); Sarune Daskeviciute-Geguziene, Jonava (LT); Yi Zhang, Sion (CH); Mohammad Khaja Nazeeruddin, Ecublens (CH)

(73) Assignees: Kaunas University of Technology, Kaunas (LT); EPFL-Swiss Federal Institute of Technology Lausanne, Lausanne (CH)

( * ) Notice: Subject to any disclaimer, the term of this patent is extended or adjusted under 35 U.S.C. 154(b) by 26 days.

(21) Appl. No.: 17/524,752

(22) Filed: Nov. 12, 2021

(65) Prior Publication Data
US 2023/0157158 A1    May 18, 2023

(51) Int. Cl.
*H01L 31/00*    (2006.01)
*C07D 209/88*   (2006.01)
(Continued)

(52) U.S. Cl.
CPC ......... *H10K 85/636* (2023.02); *C07D 209/88* (2013.01); *H01G 9/2009* (2013.01);
(Continued)

(58) Field of Classification Search
CPC .. H01G 9/2009; H01G 9/2018; H01L 51/006; H01L 51/0077; H01L 51/4253;
(Continued)

(56) References Cited

U.S. PATENT DOCUMENTS 3,684,506 A    8/1972  Guarnaccio
10,115,917 B2  10/2018 Marks et al.
(Continued)

FOREIGN PATENT DOCUMENTS

JP    2007-134502    *  5/2007
JP    2007-134502 A    5/2007

OTHER PUBLICATIONS

Subramaniam et al., Synthesis and Electrical Conductivity of Polymer Containing trans-1,2-Bis(9-Carbazolyl)cyclobutane Units, Journal of Polymer Science: Part A: Polymer Chemistry, vol. 25, 1463-1474 (1987) (Year: 1987).*

(Continued)

*Primary Examiner* — Thanh Truc Trinh
(74) *Attorney, Agent, or Firm* — Koivula & Somersalo, LLC

(57) ABSTRACT

The teachings herein pertain to hole transporting compounds containing a cyclobutyl moiety, which can be made into organic hole conductors and into hole transporting material. Additionally, optoelectronic and photoelectrochemical devices comprising such hole transporting material or hole transporting compound are described, in particular photovoltaic devices, organic-inorganic perovskite films, layered photovoltaic devices, p-n heterojunctions, dye-sensitized solar cells, organic solar cells and solid-state solar cells. Notably, a fabricated perovskite solar cell module using a disclosed HTM compound exhibited a record efficiency over 19.0% with an active area of 30.24 cm².

17 Claims, 2 Drawing Sheets

(51) Int. Cl.
*H01G 9/20* (2006.01)
*H10K 30/30* (2023.01)
*H10K 85/30* (2023.01)
*H10K 85/60* (2023.01)

(52) U.S. Cl.
CPC ............ *H01G 9/2018* (2013.01); *H10K 30/30* (2023.02); *H10K 85/30* (2023.02); *H10K 85/633* (2023.02); *H10K 85/626* (2023.02); *H10K 85/6572* (2023.02)

(58) Field of Classification Search
CPC ............ H01L 51/0058; H01L 51/0072; H10K 85/636; H10K 85/633; H10K 85/626; H10K 85/6572; H10K 30/30
See application file for complete search history.

(56) References Cited

U.S. PATENT DOCUMENTS

| | | |
|---|---|---|
| 10,115,918 B2 | 10/2018 | Qi et al. |
| 10,332,688 B2 | 6/2019 | Zhu et al. |
| 10,651,390 B2 | 5/2020 | Matsuyama et al. |
| 10,680,180 B2 | 6/2020 | Gratia et al. |
| 2015/0243444 A1* | 8/2015 | Irwin ....................... C09D 1/00 136/263 |
| 2016/0329497 A1* | 11/2016 | Radu .................... C08G 61/121 |
| 2019/0229272 A1 | 7/2019 | Getautis et al. |
| 2021/0057591 A1 | 2/2021 | Snaith et al. |

OTHER PUBLICATIONS

Xu et al., "Carbazole-Based Hole-Transport Materials for Efficient Solid-State Dye-Sensitized Solar Cells and Perovskite Solar Cells", Adv. Mater. 2014, 26, 6629-6634. (Year: 2014).*

Jacobsson et al., "Exploration of the compositional space for mixed lead halogen perovskites for high efficiency solar cells", Energy Environ. Sci., 2016, 9, 1706-1724. (Year: 2016).*

Machine translation of JP 2007-134502, pp. 1-32. (Year: 2007).*

Jolita Ostrauskite, Viktoras Voska, and Juozas V. Grazulevicius. Monatshefte fur Chemie 2002, 133, 599-607.

T. J. Jacobsson, J.P. Correa-Baena, M. Pazoki, M. Saliba, K. Schenk, M. Grätzel and A. Hagfeldt. Energy Environ. Sci., 2016, 9, 1706-1724.

J. Ostrauskite, V. Voska, G. Buika, V. Gaidelis, V. Jankauskas, H. Janeczek, J. D. Sidaravicius, and Juozas V. Grazulevicius. Synthetic Metals, 2003, 138, 457-461.

T. Jesper Jacobsson, Juan-Pablo Correa-Baena, Meysam Pazoki, Michael Saliba, Kurt Schenk, Michael Grätzel, and Anders Hagfeldt. Energy Environ. Sci., 2016,9, 1706-1724.

* cited by examiner

PHOTOVOLTAIC DEVICES CONTAINING CYCLOBUTANE-BASED HOLE TRANSPORTING MATERIALS

TECHNICAL FIELD

The present invention relates to hole transporting compounds containing a central cyclobutyl moiety, to organic hole conductors and to hole transporting material comprising such a compound, to optoelectronic or photoelectrochemical devices comprising such hole transporting material or hole transporting compound, in particular photovoltaic devices, p-n heterojunctions, dye-sensitized solar cells, organic solar cells and solid-state solar cells. The invention is also concerned with a method of preparing such organic hole conductors, layers, and photoelectrochemical devices.

BACKGROUND AND PROBLEM UNDERLYING THE INVENTION

In the recent decades, there has been a strong interest in renewable energy sources, especially the most potent among them—the sun. The conversion of solar energy to electrical current using thin film third-generation photovoltaics (PV) has been widely explored for the last two decades. The sandwich/monolithic-type PV devices, consisting of a mesoporous photoanode with an organic/inorganic light harvester, redox electrolyte/solid-state hole conductor, and counter electrode, have gained significant interest due to the ease of their fabrication, the flexibility in the selection of materials and the low cost of production.

Over the recent years, organic-inorganic hybrid perovskite solar cells (PSCs) have been attracting considerable worldwide attention due to their low cost and facile fabrication.[1] Since 2009, when Miyasaka and co-workers reported 3.8% power conversion efficiency (PCE) of PSC,[2] the performance of these photovoltaic devices has increased dramatically and currently PCE exceeds 25%.

Hole transporting materials is one of the quintessential components required for efficient PV devices. These materials are responsible for the transport of photogenerated carriers from the absorber towards the electrode. Hole transporting materials should demonstrate sufficient charge transport properties, adequate energy levels, especially its highest occupied molecular orbital (HOMO) level and good thermal stability.[3] These materials are a weak spot in the whole PV device. Despite significant research efforts devoted towards development of new hole transporting materials, the field is still dominated by 2,2',7,7'-tetrakis-(N,N-di-p-methoxyphenylamine)-9,9'-spirobifluorene (Spiro-OMeTAD) as organic hole transporting material (HTM). Unfortunately, the synthesis procedure of this HTM is a lengthy and complicated procedure requiring the use of expensive Pd catalysts, sensitive (n-butyllithium) Grignard reagents, aggressive ($Br_2$) reagents, and low temperatures (−78° C.).[4] Furthermore, to ensure maximum performance, Spiro-MeOTAD must be purified via sublimation, inevitably driving up the cost of the material.

As the synthesis of Spiro-OMeTAD is extremely expensive, the development of low-cost and efficient HTMs remains a crucial challenge for large scale applications. Synthetic work undertaken to replace Spiro-MeOTAD has yielded several groups of HTM molecules demonstrating good charge mobility and comparable performance in the PV devices, however a vast majority of these derivatives still require expensive catalysts and multistep synthesis procedures.

The synthesis process of previously discovered hole transporting material involves expensive starting material compounds that are not commercially available, very low reaction temperatures, aggressive reagents, and complex reaction steps (e.g. 5 steps for the Spiro-OMetTAD synthesis). Thus, the synthesis process is lengthy, time-consuming, and expensive and causes non-negligible environmental impact. The presented invention provides a hole transport material that can be used in a high efficiency solar cell, can be prepared using a minimal number of industrially scalable steps and readily available or low-cost materials, which keeps the material costs and impact on the environment very low.

Carbazole is known to be a promising core unit for molecular design since it can be substituted with a wide range of desired groups, allowing fine-tuning of optical and electrochemical properties.[5] Various carbazole-containing scaffolds as electron donating units in the periphery were routinely used to tune the HOMO level and applied in PSCs, showing comparable photovoltaic performance.[6-8] This includes star-shaped SGT series,[9,10] benzodithiazole,[11] bismethylenebenzene,[12,13] bipyridine,[14] pyrene-based[15] examples. Photodimerized carbazole is an attractive building block due to the simple, elegant and green synthesis and has been studied as excimer-free and high hole carrier mobility material in early works.[16-18]

Herein, we disclose the development of novel HTMs, which comprise cyclobutane as a new structural core element for HTMs flanked by two differently substituted, photodimerized carbazole arms in a branched fashion. The specific arrangement of carbazolyl groups onto cyclobutane core is also likely to facilitate the carrier transport process. Moreover, bulkiness and sterically hindered rigid transconfiguration result in competition between the planarization and repulsive steric hindrance leading to a pseudo spiro type arrangement and diversified torsion angles. The effects of different peripheral carbazole substituents on various properties of newly synthesized molecules have been systematically investigated. Novel cyclobutane-based HTMs have been successfully applied in PSCs, showing PCE up to 21% and improved long-term stability under atmospheric environment comparing to spiro-OMeTAD. Most importantly, to obtain novel HTMs we have applied protocols inspired by green chemistry, for the first time presenting that HTMs for PSCs could be synthesised eliminating the use of hazardous substances to reduce the adverse environmental impact without sacrificing the efficiency.

SUMMARY OF THE INVENTION

The purpose of present invention is to provide new hole transporting organic compounds with suitable energetic levels, which do not require a sublimation step for purification after its synthesis as is the case of the synthesis of Spiro-OMeTAD.

The present teachings also provide new hole transporting materials, which provide higher power conversion efficiency (PCE) to photovoltaic devices comprising perovskite, organic, or organometallic dyes as sensitizer.

DETAILED DESCRIPTION OF THE INVENTION

Figure 1:
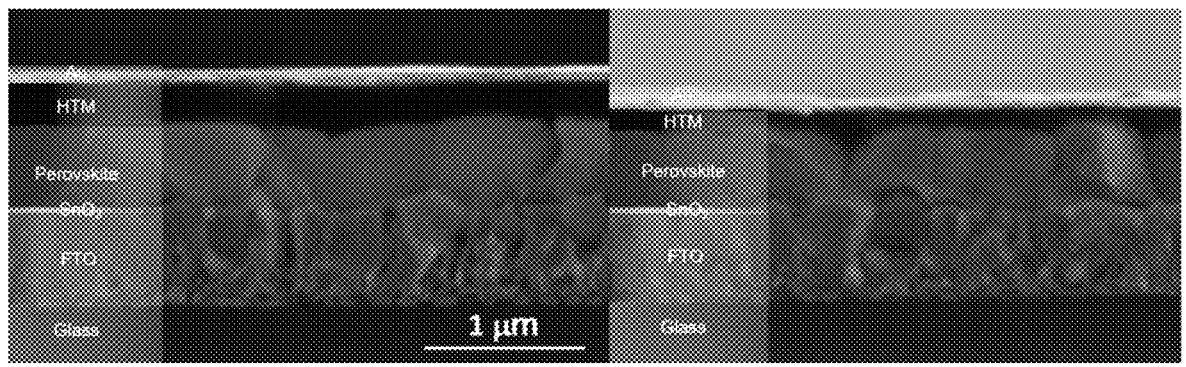
FIG. 1 shows a microscopic image of a cross-sectional view of a sample photovoltaic cell comprising FTO/$SnO_2$/perovskite/Spiro-OMeTAD/Au (left) and FTO/$SnO_2$/perovskite/cyclobutyl-HTM/Au (right).

The main object of these teachings is new compounds of formula (I) containing a cyclobutane moiety:

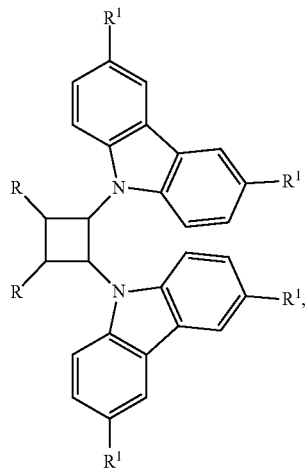

(I)

wherein

R, $R^1$ is a mono- or polycyclic system comprising at least one pair of conjugated double bonds (—C=C—C=C—), the polycyclic system comprising fused aromatic rings or monocyclic aromatic rings bound together by covalent bonds or heteroaromatic system with N, O, S, Se, Si heteroatoms. Said mono- or polycyclic system being substituted by H, halogen, cyano group, C1-C20 cyanoalkyl group, C1-C20 alkyl, C1-C20 alkoxy group, C1-C20 alkoxyalkyl, C1-C20 haloalkyl group, C1-C20 haloalkoxyalkyl, wherein said cyanoalkyl, alkyl, alkoxy, alkoxyalkyl, haloalkyl, haloalkoxyalkyl, C4-C20 aryl, C4-C20 alkylaryl, C4-C20 alkoxyaryl C4-C20 alkenylarylalkyl, C4-C20 alkoxyarylalkenyl, C4-C20 bisalkoxyarylalkenyl groups, if they comprise 3 or more carbons, may be linear, branched or cyclic; and wherein halogen is selected from Cl, F, Br, or I;

According to another embodiment, the hole transporting compounds of formula (I) containing cyclobutyl moiety is selected from, but not limited to, a compound according to any one of formulae (1) to (52):

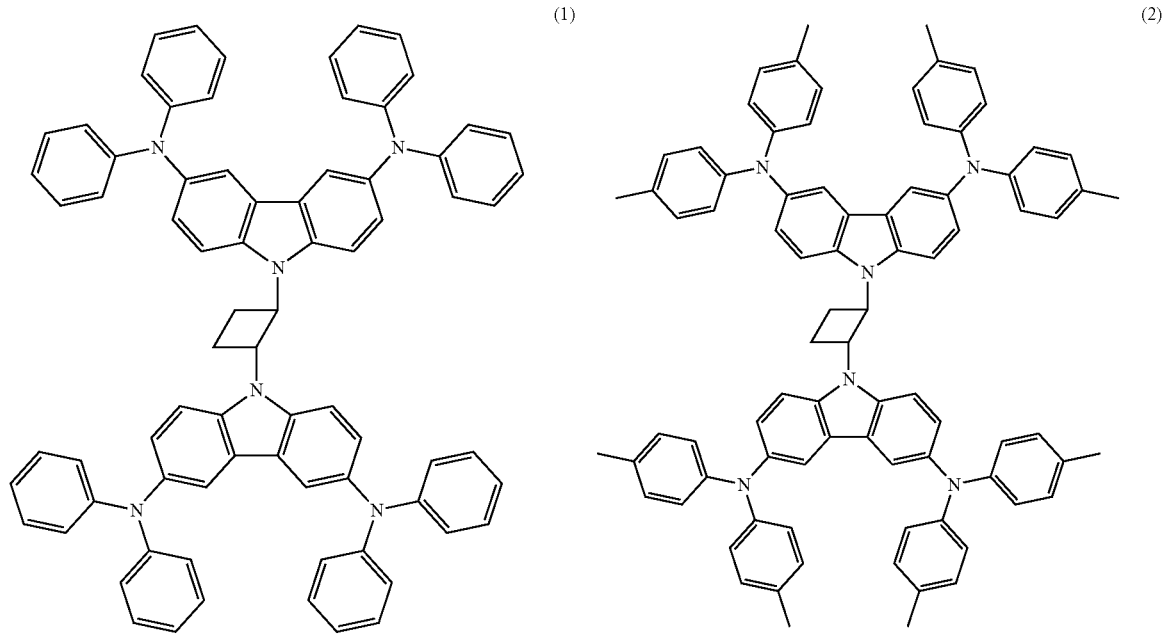

(3)
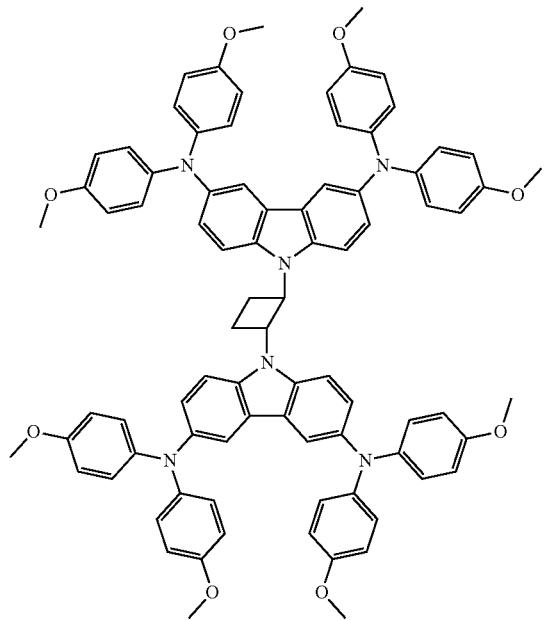
(4)
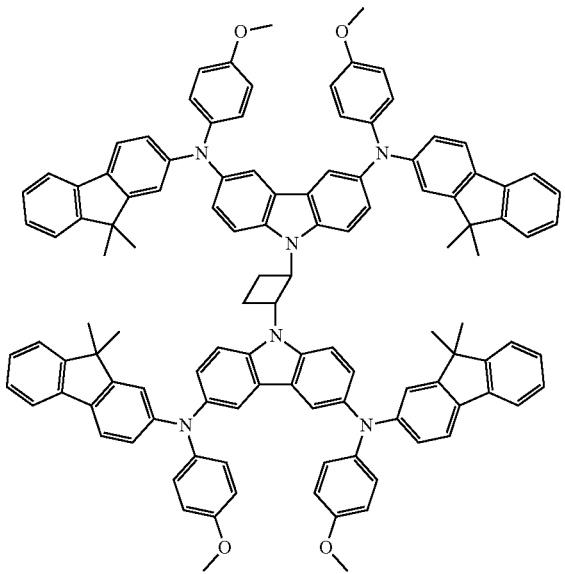
(5)
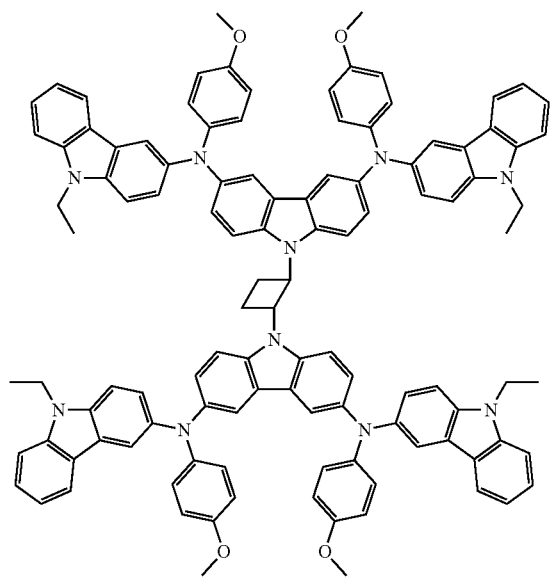
(6)
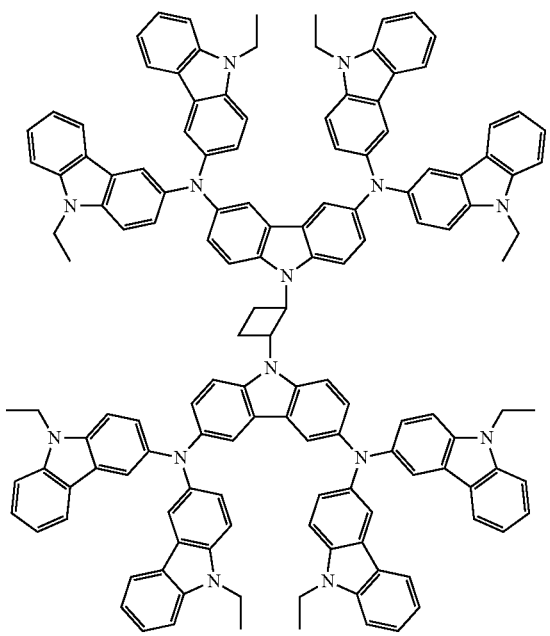

(7)
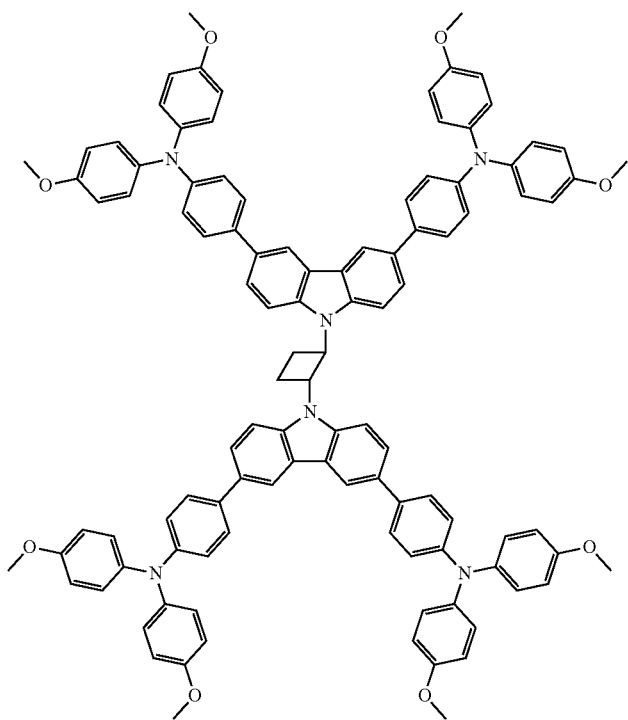
(8)
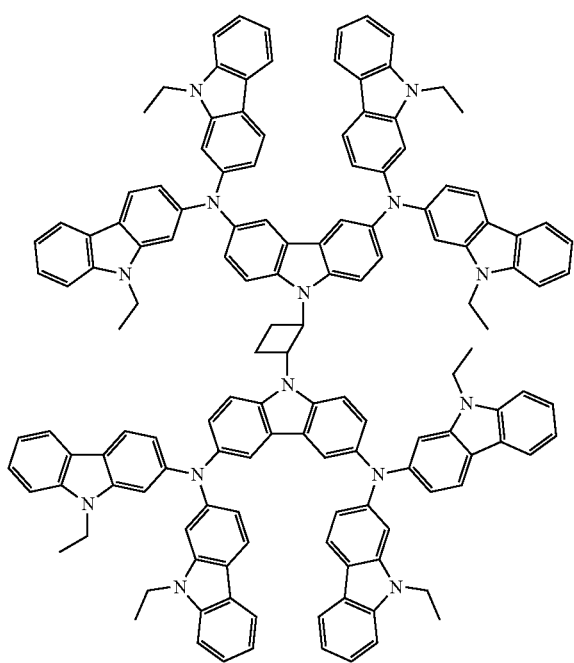

(9)
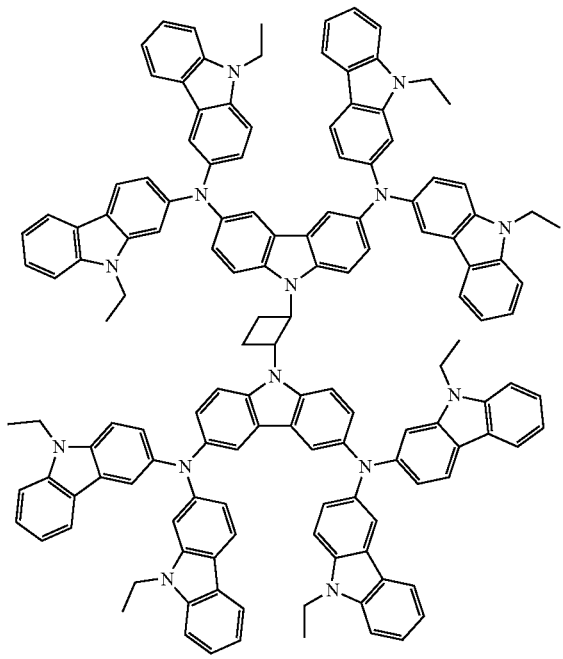
(10)
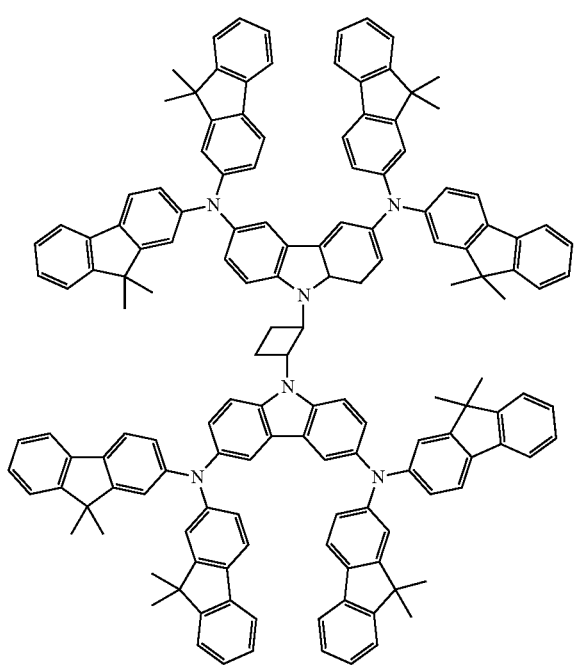

-continued
(11)
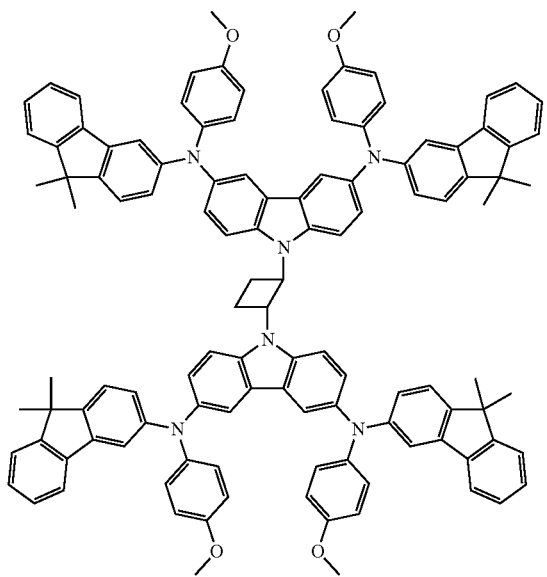
(12)
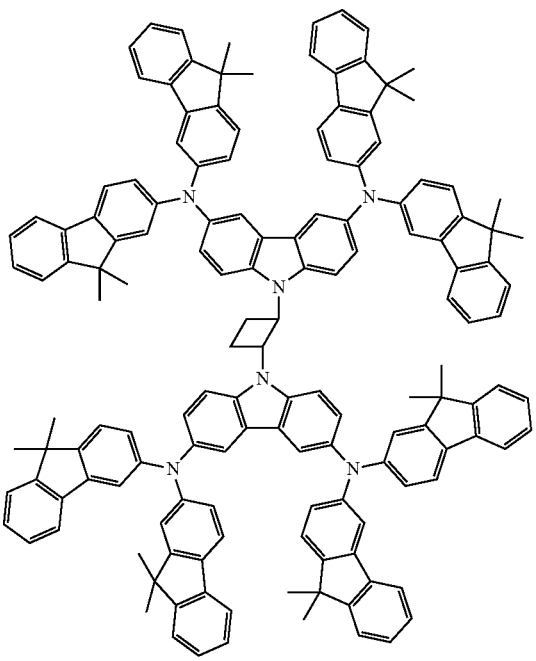
(13)
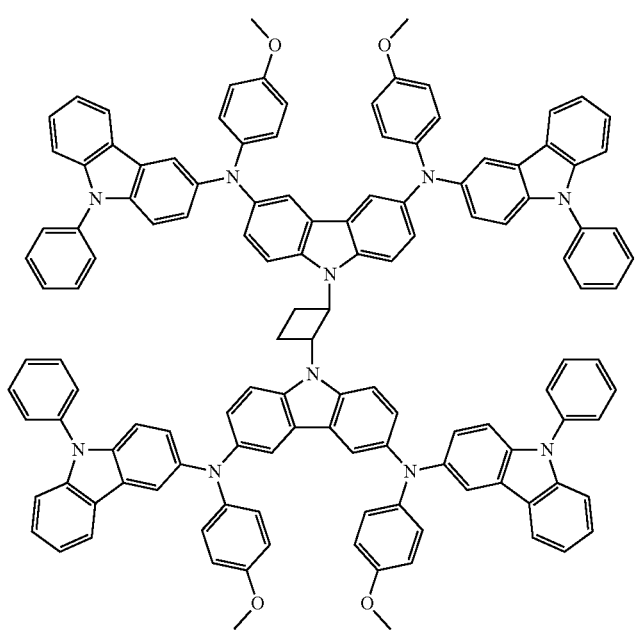

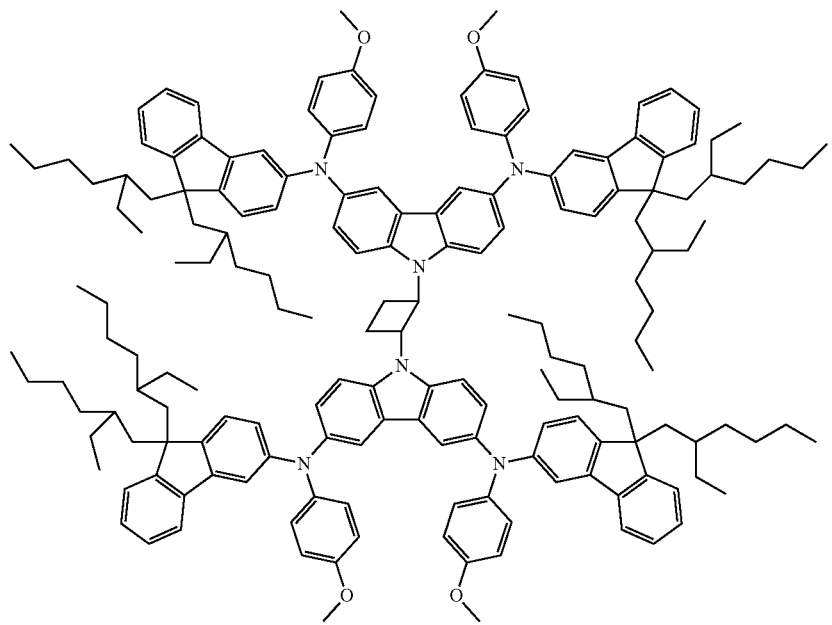
(14)
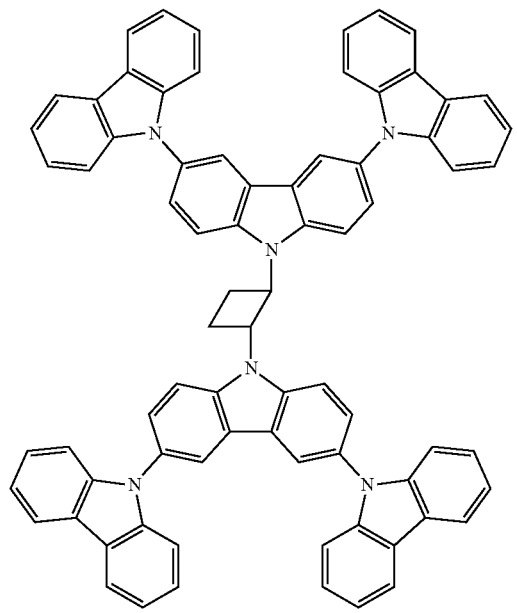
(15)
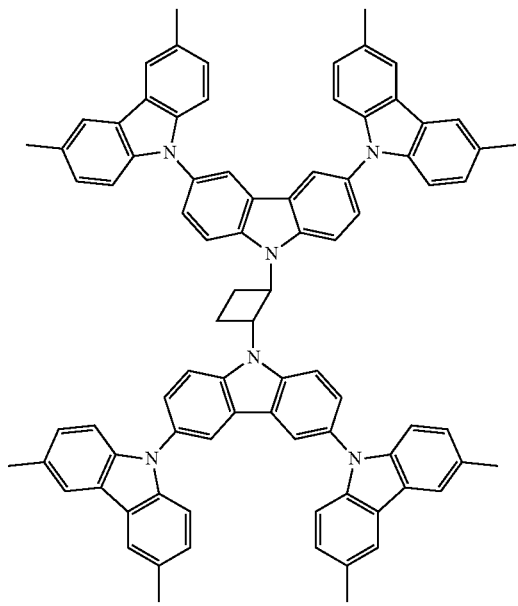
(16)

-continued
(17)
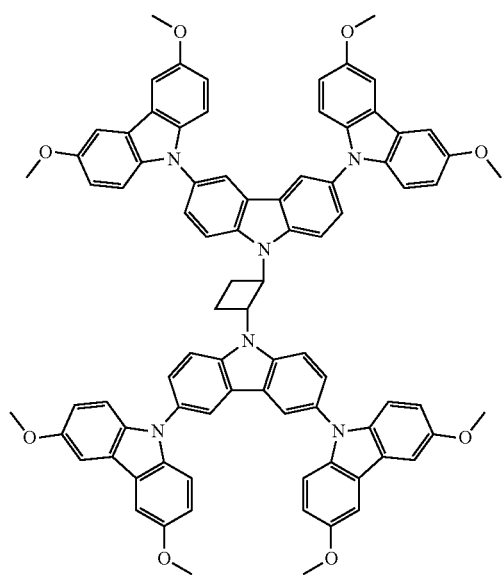
(18)
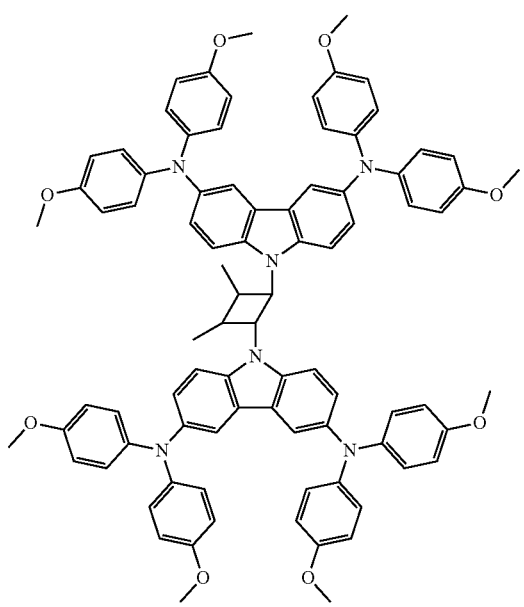
(19)
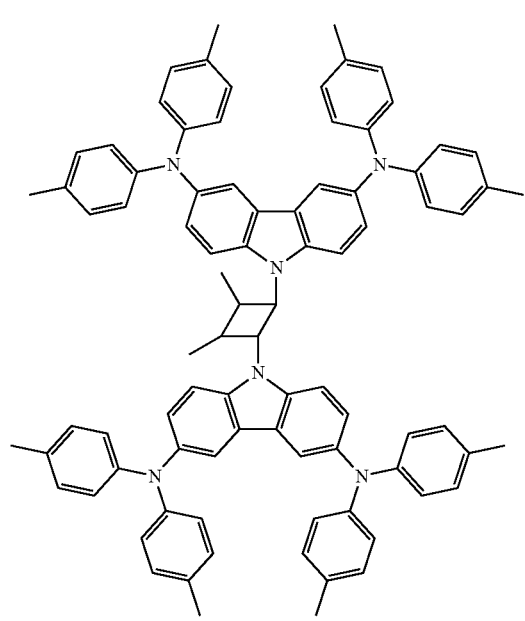
(20)
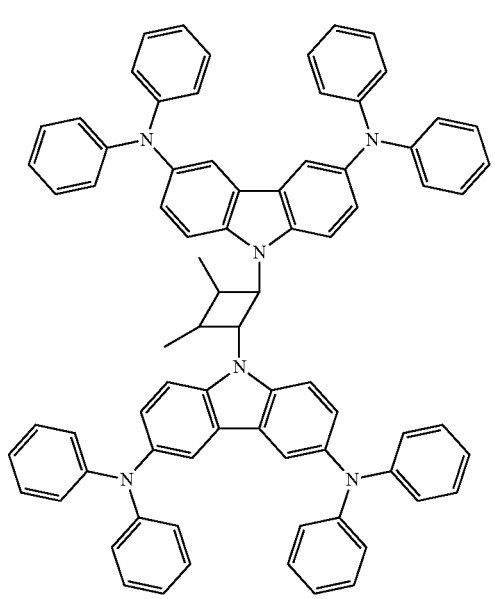

(21)
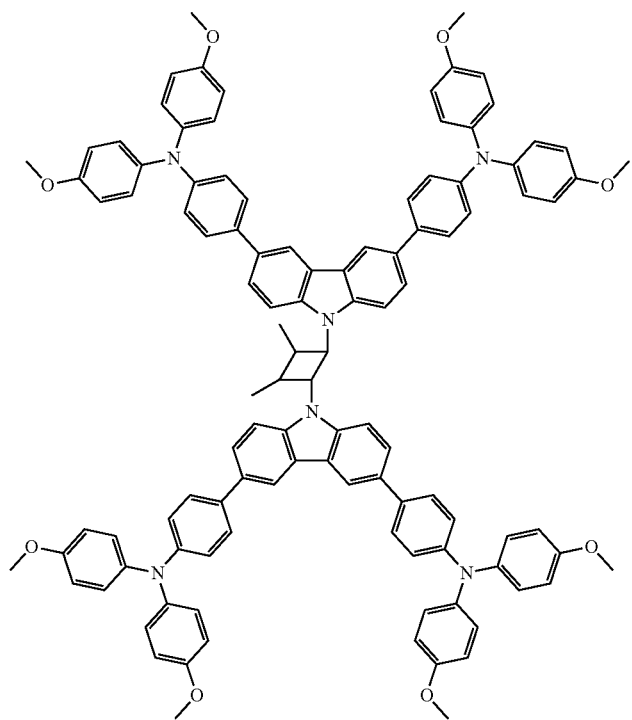
(22)
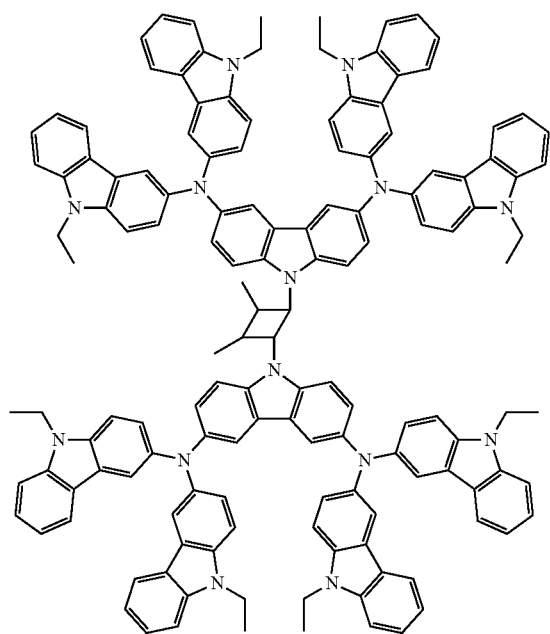

(23)
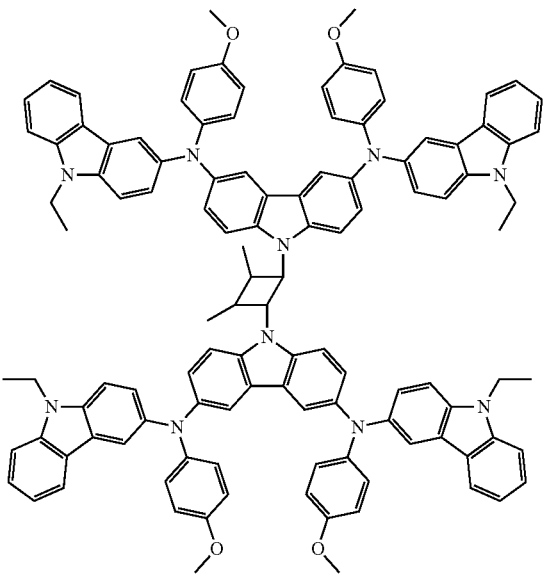
(24)
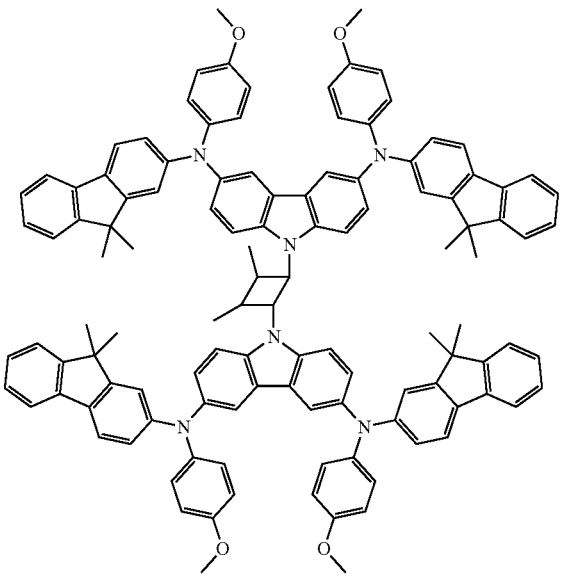
(25)
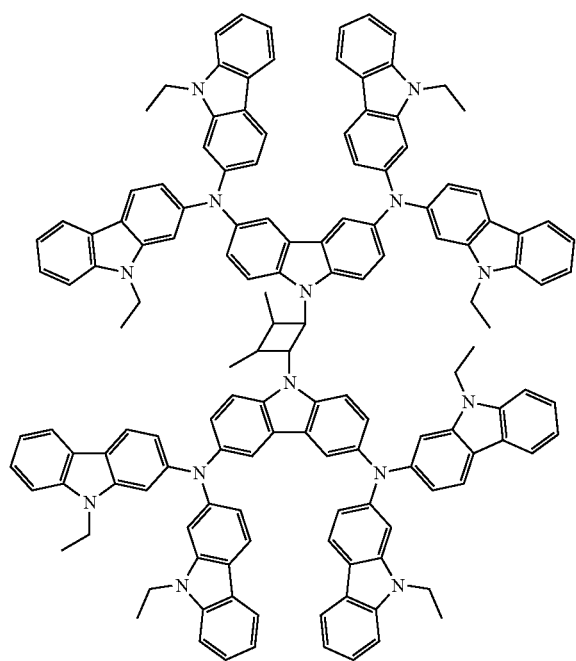

-continued
(26)
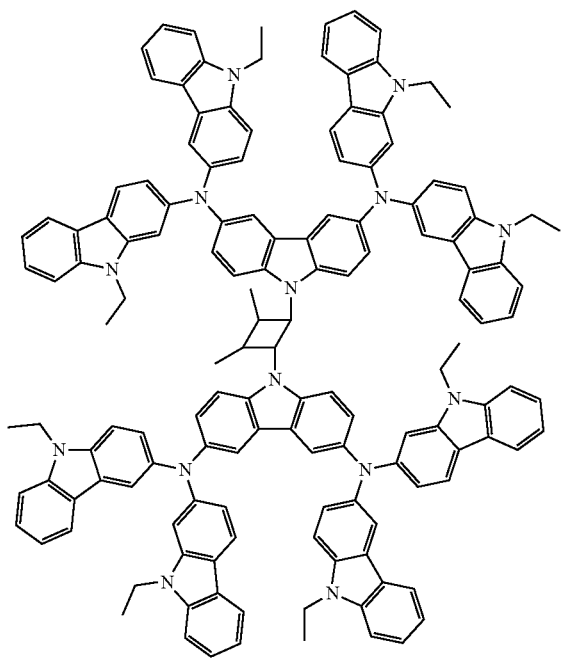
(27)
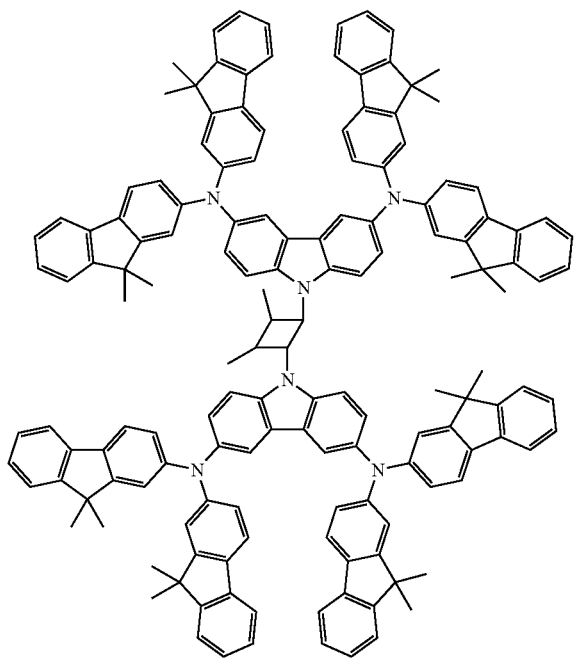

(28)
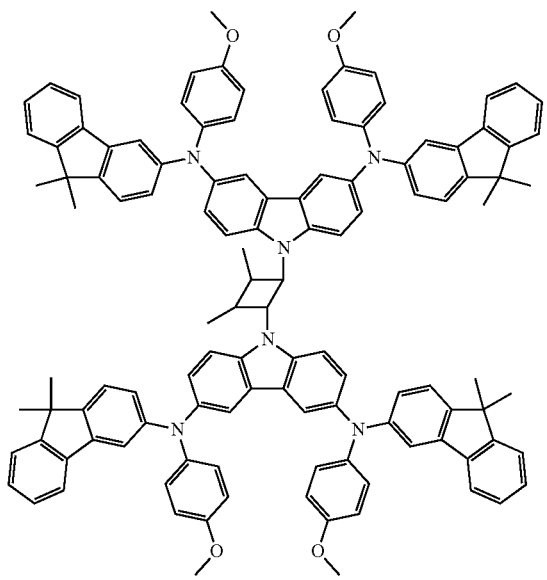
(29)
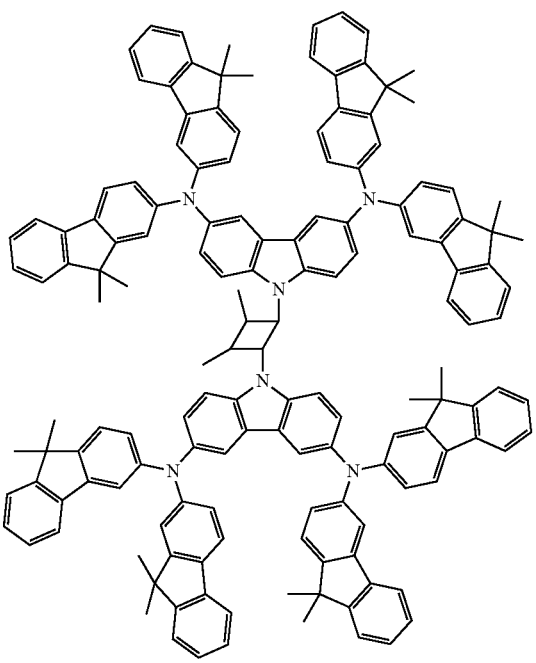
(30)
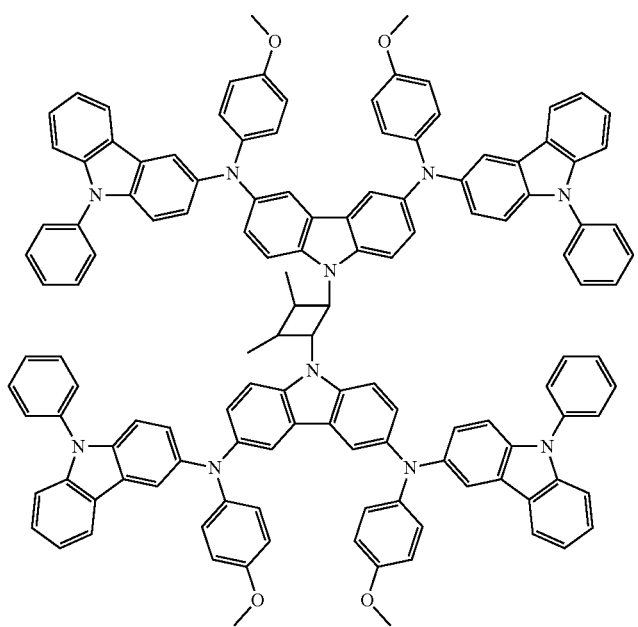

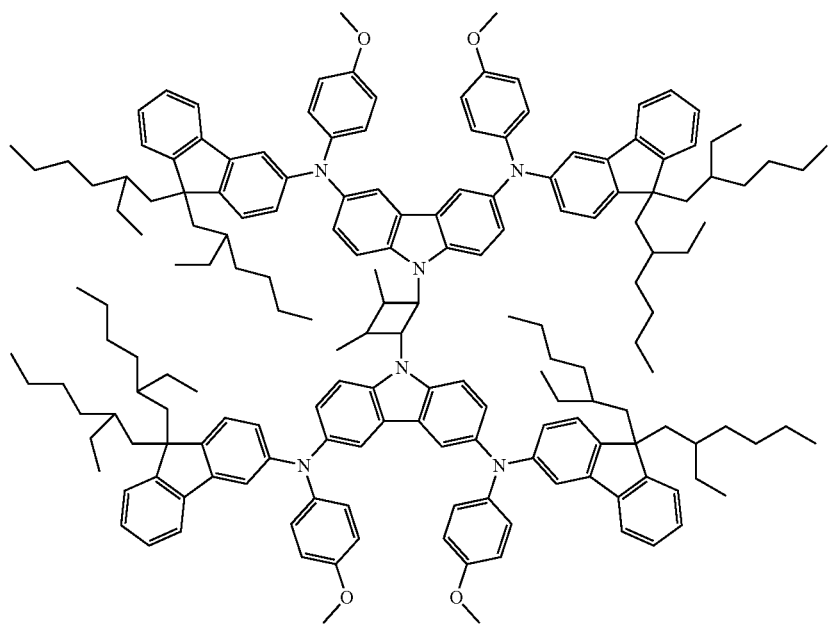
(31)
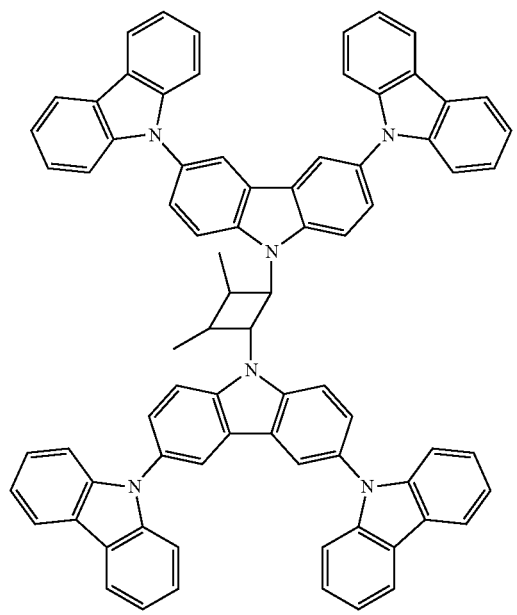
(32)
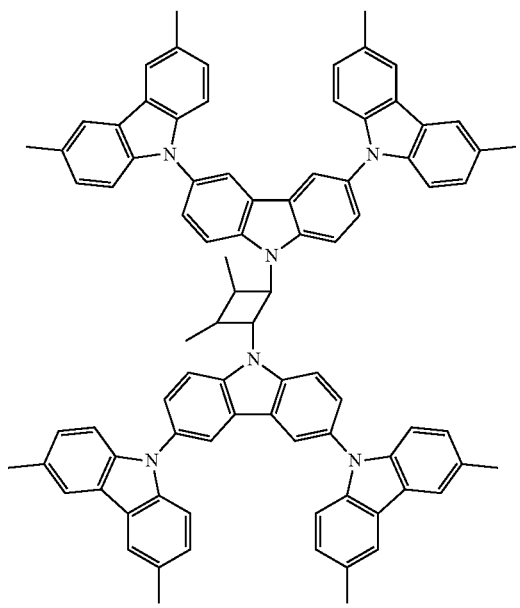
(33)

-continued
(34)
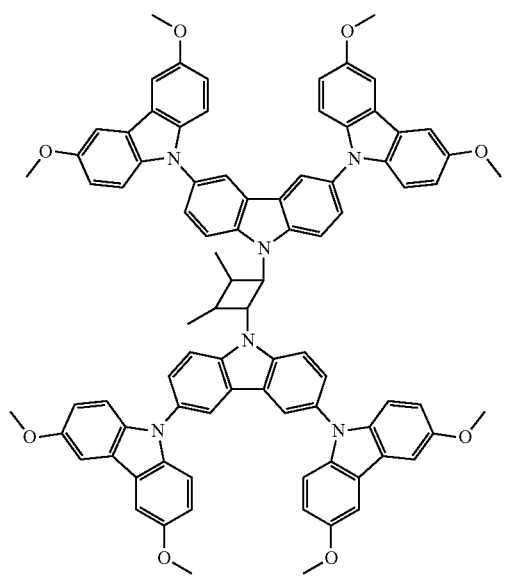
(35)
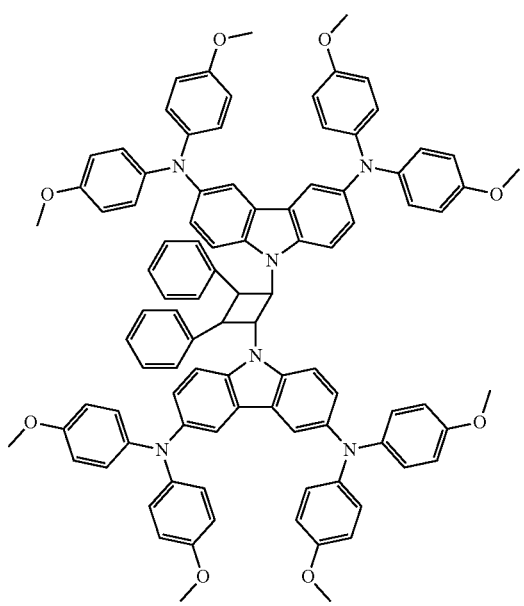
(36)
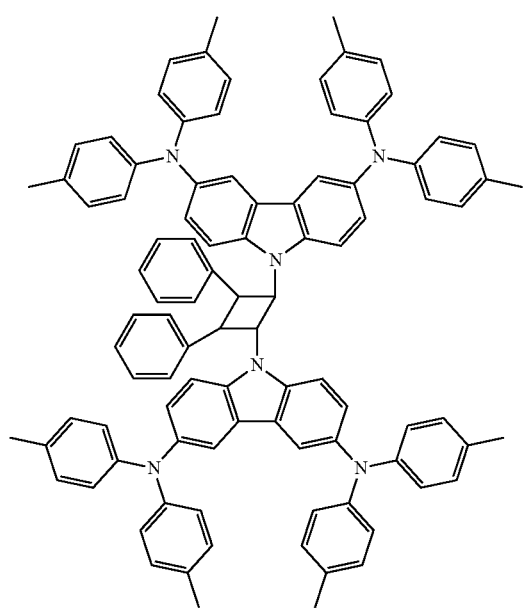
(37)
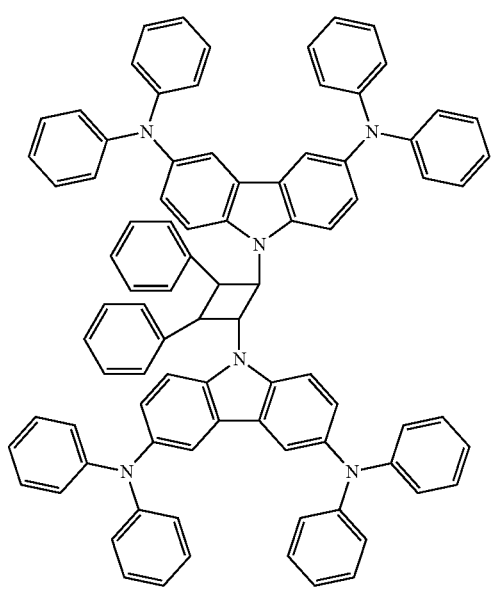

(38)
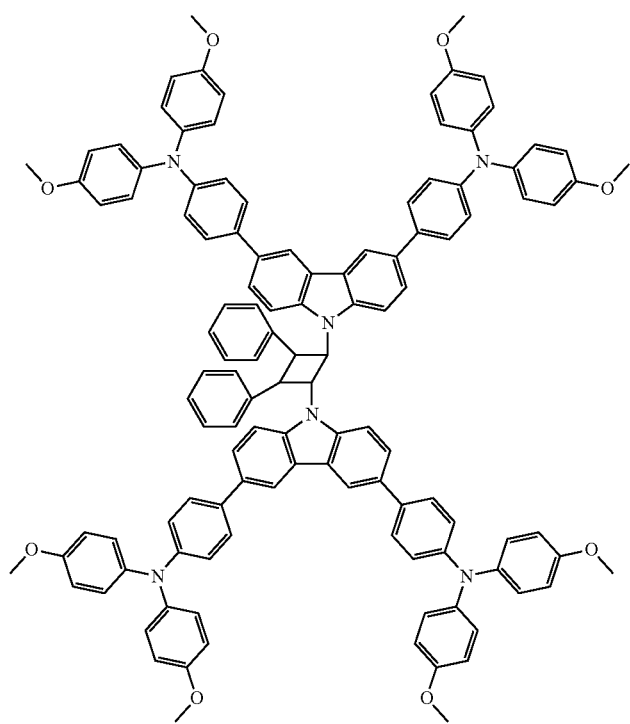
(39)
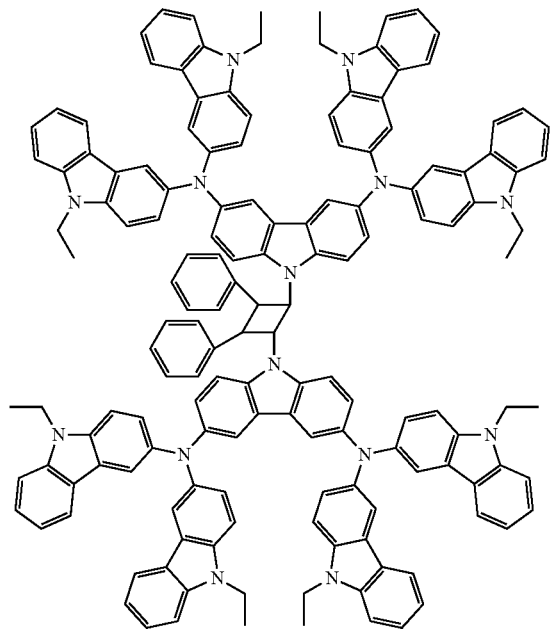

-continued
(40)
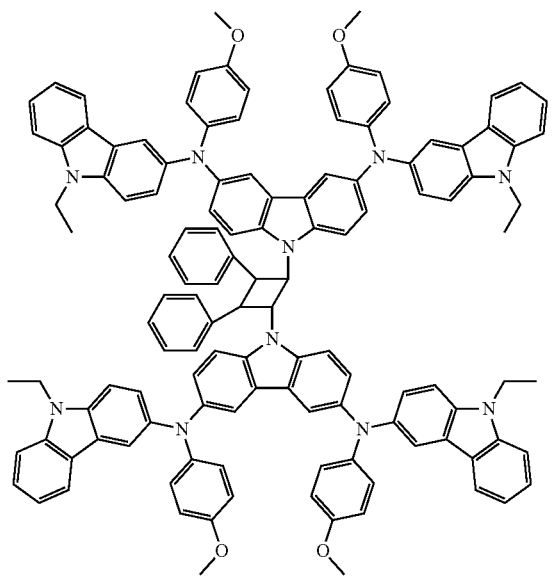
(41)
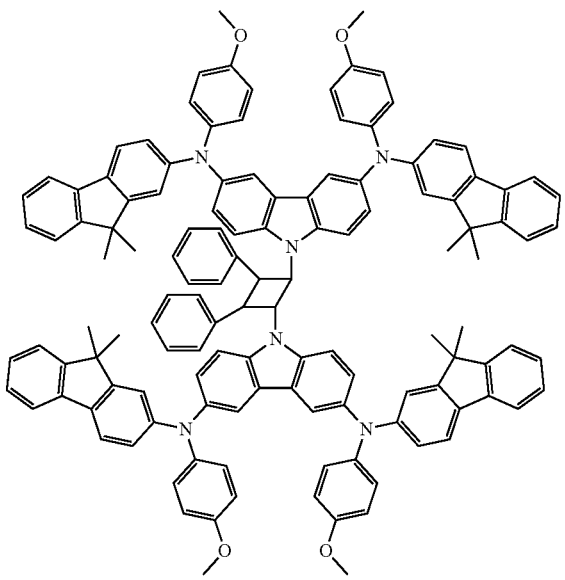
(42)
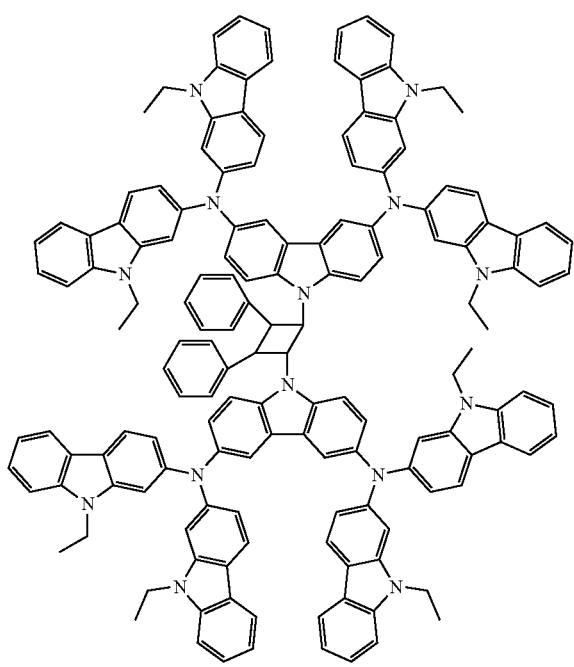

(43)
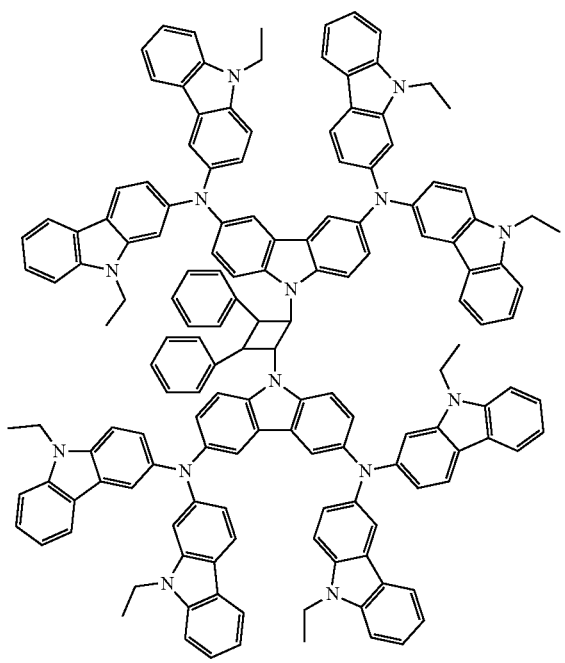
(44)
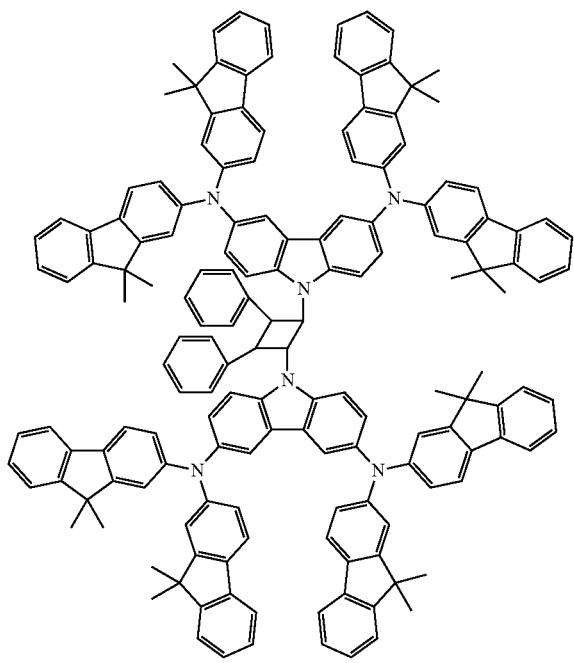

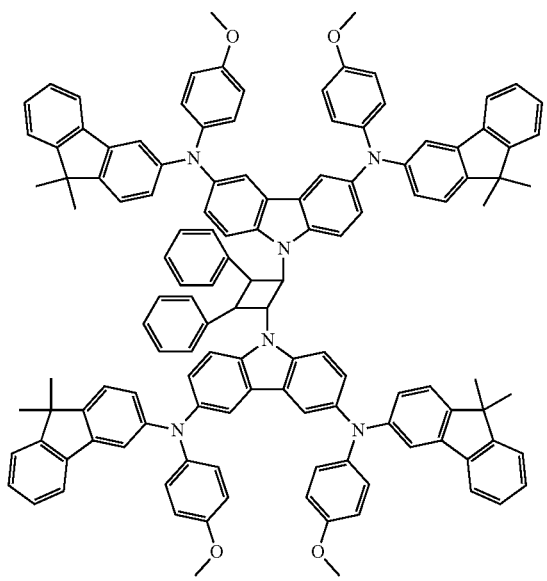
(45)
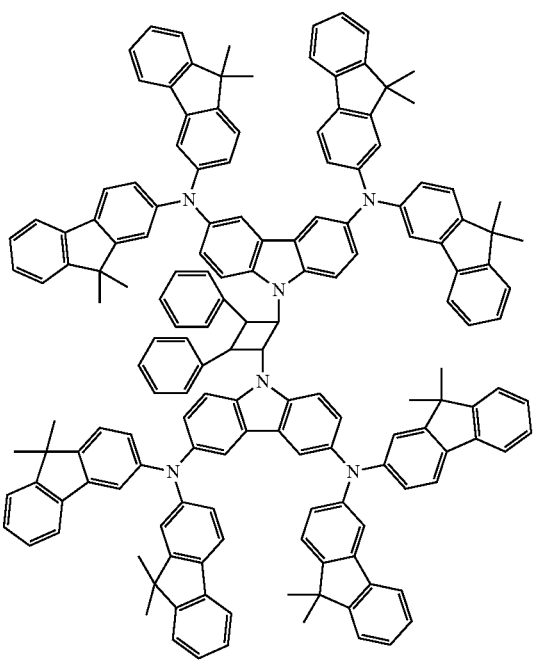
(46)
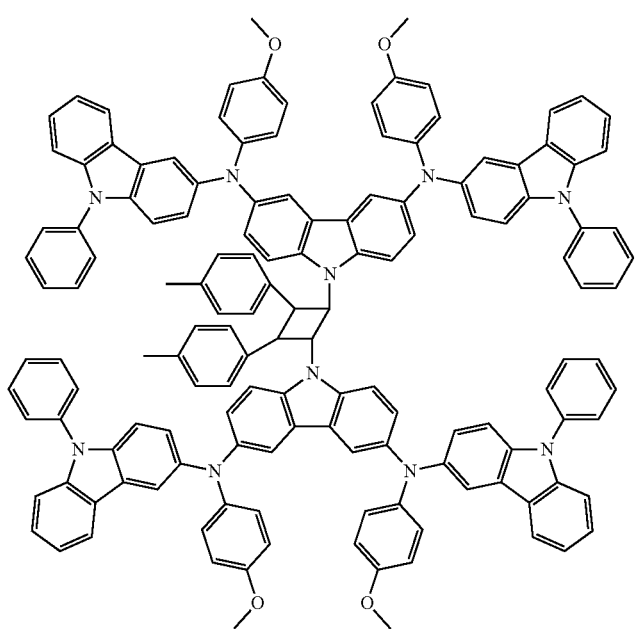
(47)

(48)
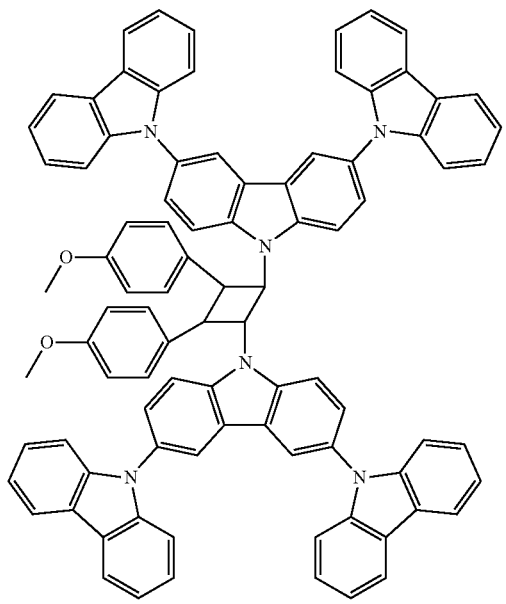
(49)
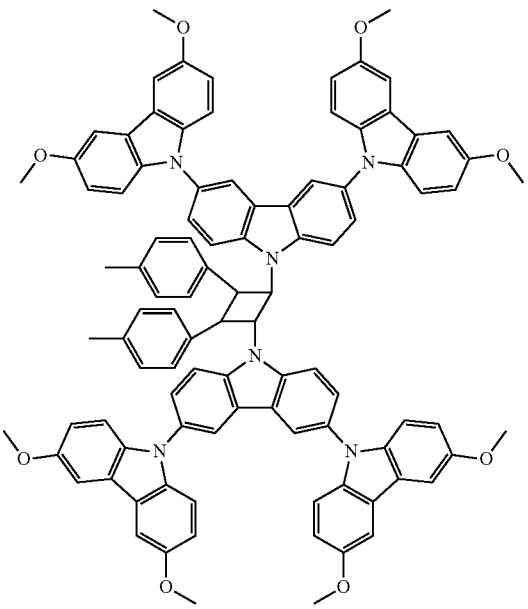
(50)
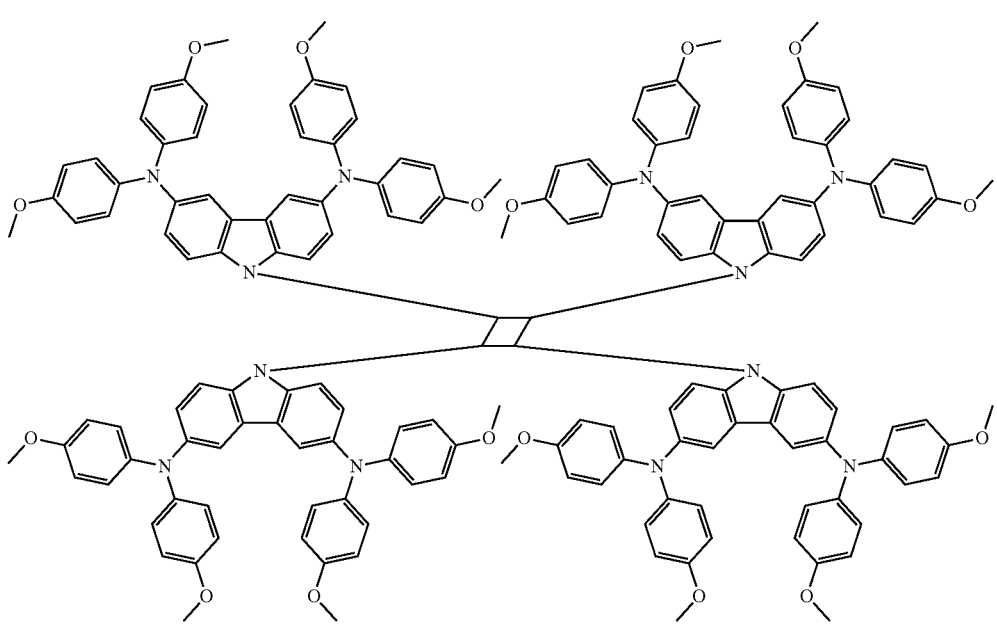

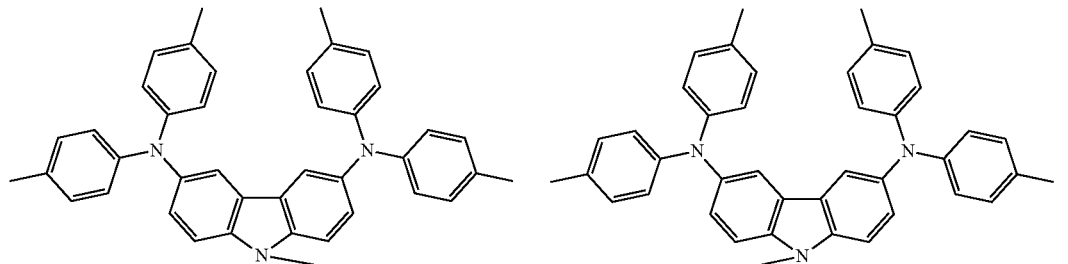

(51)

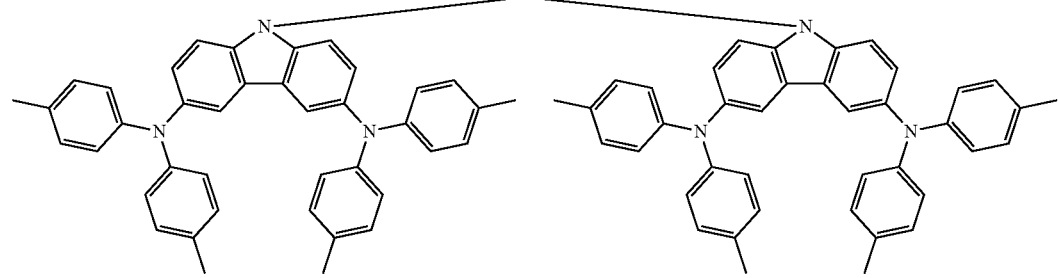

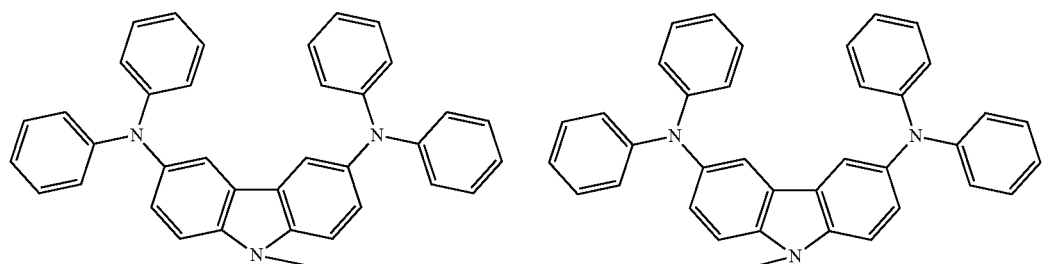

(52)

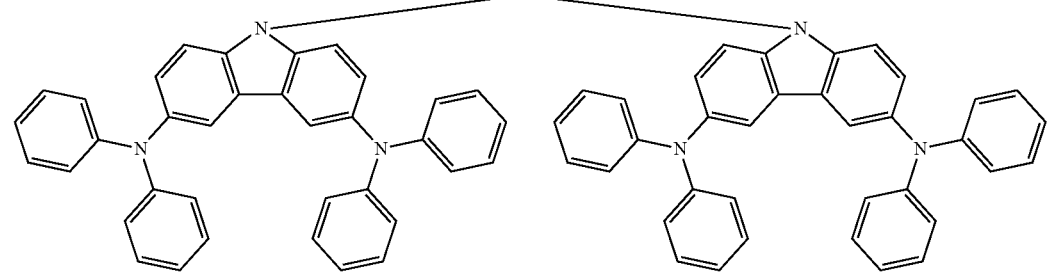

In yet another embodiment, the invention provides a hole transporting material comprising at least one molecule with hole transporting properties and combination of two or more of the aforementioned being selected from a compound of formula (I). Said compounds of the general formula (I) are for use as an organic non-polymeric semiconductor. More specifically, the invention provides hole transporting material selected from at least one compound of the general formula (I).

The invention also provides, in another embodiment, an optoelectronic and/or photoelectrochemical device comprising a compound of formula (I). The optoelectronic and/or photoelectrochemical device comprises a hole transporting material, wherein said hole transporting material comprises a compound of formula (I).

The optoelectronic and/or photoelectrochemical device is selected from an organic photovoltaic device, a photovoltaic solid-state device, a p-n heterojunction, an organic solar cell, a dye sensitized solar cell, or a solid-state solar cell.

In the preferred embodiment, the optoelectronic and/or photoelectrochemical device, in particular a photovoltaic solid-state device, comprises a conducting support layer, a surface-increasing scaffold structure or electron transporting layer, a sensitizer or sensitizer layer, a hole transporting layer comprising a cyclobutyl-based compound of formula (I), a counter electrode, and/or metal layer. Further, the optoelectronic and/or photoelectrochemical device is a photovoltaic solid-state device being a solid-state solar cell comprising an organic-inorganic perovskite as sensitizer.

According to another embodiment, the optoelectronic and/or photoelectrochemical device is a solar cell selected from an organic solar cell, a dye sensitized solar cell, or a solid-state device.

In still another embodiment, the hole transporting layer of the optoelectronic and/or photoelectrochemical device, in particular a photovoltaic solid-state device, is made of a hole transporting material comprising at least one small molecule hole transporting material being selected from a compound of formula (I).

The conducting support layer is preferably substantially transparent. "Transparent" means transparent to at least a part, preferably a major part of the visible light. Preferably, the conducting support layer is substantially transparent to all wavelengths or types of visible light. Furthermore, the conducting support layer may be transparent to non-visible light, such as UV and IR radiation, for example.

The conducting support layer preferably functions and/or comprises a current collector, collecting the current obtained from the photovoltaic solid-state device. The conducting support layer may comprise a material selected from indium doped tin oxide (ITO), fluorine doped tinoxide (FTO), $ZnO$—$Ga_2O_3$, $ZnO$—$Al_2O_3$, tin-oxide, antimony doped tin oxide (ATO), $SrGeO_3$ and zinc oxide, preferably coated on a transparent substrate, such as plastic or glass. In this case, the plastic or glass provides the support structure of the layer, and the cited conducting material provides the conductivity. Such support layers are generally known as conductive glass and conductive plastic, respectively, and are preferred conducting support layers in accordance with the invention.

According to another embodiment, the surface area-increasing scaffold structure is nanostructured and/or nanoporous. The scaffold structure is thus preferably structured on a nanoscale. The structures of said scaffold structure increase the effective surface area compared to the surface area of the conductive support. Said scaffold structure is made from and/or comprises a metal oxide as electron transporting material. For example, the material of the scaffold structure is selected from semiconducting materials, such as Si, $TiO_2$, $SnO_2$, $Fe_2O_3$, $ZnO$, $WO_3$, $Nb_2O_5$, $CdS$, $ZnS$, $PbS$, $Bi_2S_3$, $CdSe$, $CdTe$, $SrTiO_3$, $GaP$, $InP$, $GaAs$, $CuInS_2$, $CuInSe_2$, or combinations thereof.

According to one embodiment, the sensitizer layer of the photovoltaic solid-state device comprises at least one pigment being selecting from organic, inorganic, organometallic, organic-inorganic pigments, or a combination thereof. The sensitizer is preferably a light absorbing compound or material. Preferably, the sensitizer is a pigment, and most preferably the sensitizer is an organic-inorganic pigment. The sensitizer layer may comprise one or more pigments of the group consisting of organometallic sensitizing compounds, metal free organic sensitizing compounds, inorganic sensitizing compounds such as quantum dots, aggregates of organic pigments, nanocomposites, in particular organic-inorganic perovskites, and combinations of the aforementioned. For the purposes of this invention, it is in principle possible to use any type of dyes or sensitizer, including combinations of different types of dyes or different dyes of the same type.

According to the preferred embodiment, the sensitizer layer of the photovoltaic solid-state device is coated by a layer comprising a compound of formula (I). Preferably said sensitizer layer comprises an organic-inorganic perovskite.

According to the preferred embodiment, the sensitizer or the sensitizer layer comprises, consists of, or is made of an organic-inorganic perovskite. Said organic-inorganic perovskite is provided under a film of one perovskite pigment or mixed perovskite pigments or perovskite pigments mixed with further dyes or sensitizers.

According to a further embodiment, the sensitizer layer comprises another pigment in addition to the organic-inorganic perovskite pigment, said another pigment selected from organic pigment, organometallic pigment, or inorganic pigment.

According to another embodiment, the optoelectronic and/or photoelectrochemical device is a dye sensitized solar cell (DSC) comprising a compound of formula (I) as hole transporting material and a pigment as sensitizer selected from organic pigment, organometallic pigment, inorganic pigment, or a combination thereof.

The term "perovskite", for the purpose of this specification, refers to the "perovskite structure" and not specifically to the perovskite material, $CaTiO_3$. For the purpose of this specification, "perovskite" encompasses and preferably relates to any material that has the same type of crystal structure as calcium titanium oxide and of materials in which the bivalent cation is replaced by two separate monovalent cations. The perovskite structure has the general stoichiometry $AMX_3$, where "A" and "M" are cations and "X" is an anion. The "A" and "M" cations can have a variety of charges, for instance, in the original Perovskite mineral ($CaTiO_3$), the A cation is divalent, and the M cation is tetravalent.

In a further embodiment, the organic-inorganic perovskite layer material comprises a perovskite-structure of formula (II):

$$AMX_3 \quad\quad\quad (II)$$

wherein

A is an alkali metal ion, preferably $Li^+$, $Na^+$, $K^+$, $Rb^+$, $Cs^+$; ammonium or amidinium ion, wherein one or more hydrogens are substituted by alkyl or acyl group. Said ammonium ions, including mono, di, tri and tetra alkyl ammonium ions, wherein one or more hydrogens are substituted by alkyl group. Preferably, the substituent is alkyl group or groups independently selected from C1-C6, preferably methyl or ethyl groups. Said ammonium ions, N-alkyl amidinium and imidinium ions, wherein one or more hydrogens are substituted by alkyl group. Preferably, the amidinium or imidinium ions are selected from C1-C6 carboxamide groups, preferably formamidium or acetamidium groups. The hydrogen atoms in the organic cations, A, may be substituted by halogens selected from F, Cl, I and Br, preferably F or Cl. Preferably, A is $Cs^+$ or methyl ammonium ion ($MA^+$), or formamidium ion ($FA^+$).

M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$; preferably $Pb^{2+}$, $Sn^{2+}$.

X is monovalent anion, independently selected from the group consisting of $Cl^-$, $Br^-$, $I^-$, $NCS^-$, $CN^-$, and $NCO^-$; preferably $Cl^-$, $Br^-$, or $I^-$. X may be the same or different.

According to the preferred embodiment, the examples of organic-inorganic perovskites are: methyl ammonium lead halides, for example, methylamonium lead iodide (CH3NH3PbI3); methylamonium lead mixed halides, for example, CH3NH3PbCII2; formamidium lead halides, for example, HC(NH2)2PbI3, HC(NH2)2PbBr3 or HC(NH2)2PbCl2I; cesium lead iodide (CsPbI3), cesium tin iodide (CsSnI3).

In a further embodiment, the organic-inorganic perovskite layer material comprises a mixed perovskite-structure, wherein A is the mixture of two or more cations as defined above, X is the mixture of two or more anions as defined above. Preferably, A is the mixture of two cations, M is Pb and X is a mixture of two anions. The formula (II) may be expressed as formula (III) below:

$$A^1{}_{1-y}A^2{}_yPbX^1{}_{3-z}X^2{}_z \qquad (III)$$

wherein:
A$^1$ and A$^2$ are organic monovalent cations as defined above for A;
X$^1$ and X$^2$ may be the same or different monovalent anions selected from the group
consisting of Cl$^-$, Br$^-$, I$^-$, NCS$^-$, CN$^-$ and NCO$^-$;
y is in the interval between 0.1 and 0.9;
z is in the interval between 0.2 and 2.

General Synthesis Scheme of Compounds of General Formula (I).

Hole transporting compounds containing cyclobutane moiety corresponding to the general formula (I) were prepared by the three-step synthesis route shown in Scheme 1. The first step was the photochemical cyclodimerization of commercially obtained 9H-vinylcarbazole (Sigma-Aldrich) according to Ref. (J. Polym. Sci. A 1987, 25, 1463) followed by bromination of the precursor A (Monatshefte Für Chemie—Chemical Monthly. 1971, 102, 711) to obtain 1,2-bis (3,6-dibromo-9H-carbazol-9-yl)cyclobutane (B). The last step was the Buchwald-Hartwig cross coupling reaction of intermediate B with bis(4-methoxyphenyl)amine, bis(4-methylphenyl)amine or diphenylamine provided the target compounds 1-3. Compounds 4-6 were synthesized according to this method. N-(4-methoxyphenyl)-9,9-dimethyl-9H-fluoren-2-amine, 9-ethyl-N-(4-methoxyphenyl)-9H-carbazol-3-amine and bis(9-ethyl-9H-carbazol-3-yl)amine instead of the diphenylamine derivative was used in the last step in the case of compound 4, 5, and 6, accordingly.

Scheme 1. Synthesis route to the hole transporting materials 1-3

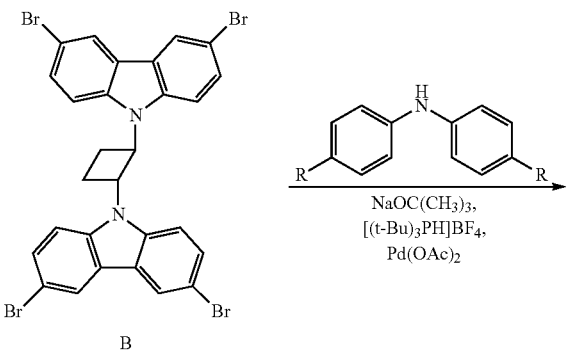

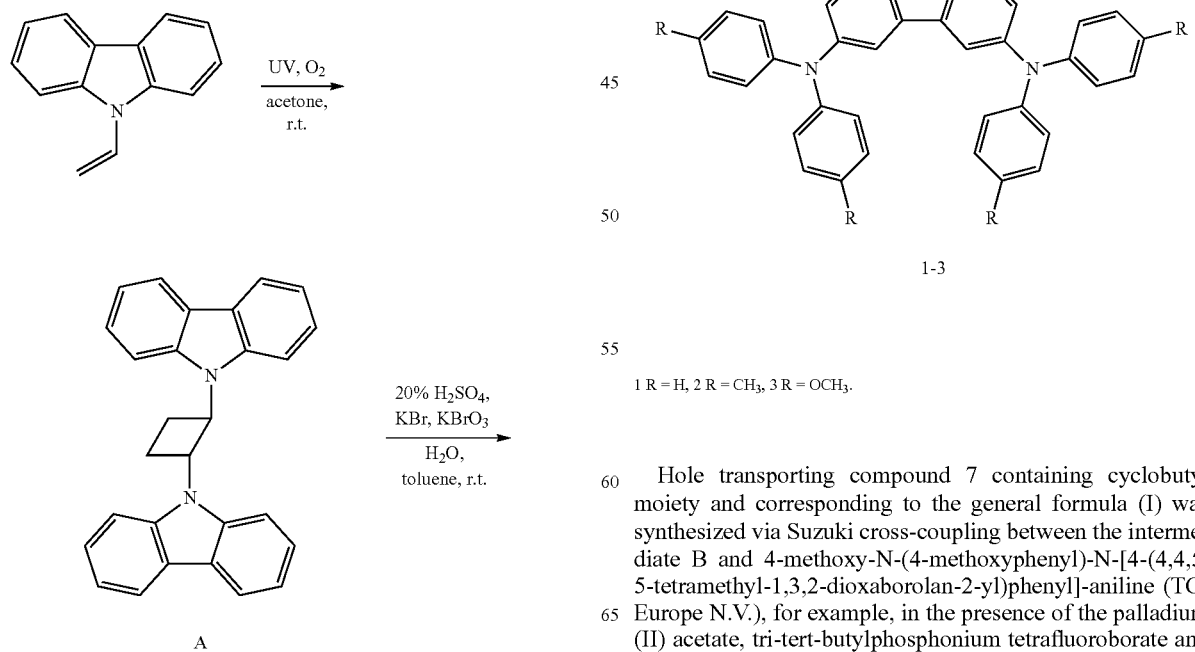

1 R = H, 2 R = CH$_3$, 3 R = OCH$_3$.

Hole transporting compound 7 containing cyclobutyl moiety and corresponding to the general formula (I) was synthesized via Suzuki cross-coupling between the intermediate B and 4-methoxy-N-(4-methoxyphenyl)-N-[4-(4,4,5,5-tetramethyl-1,3,2-dioxaborolan-2-yl)phenyl]-aniline (TCI Europe N.V.), for example, in the presence of the palladium (II) acetate, tri-tert-butylphosphonium tetrafluoroborate and sodium tert-butoxide (Scheme 2):

Scheme 2. Synthesis route to the hole transporting material 7

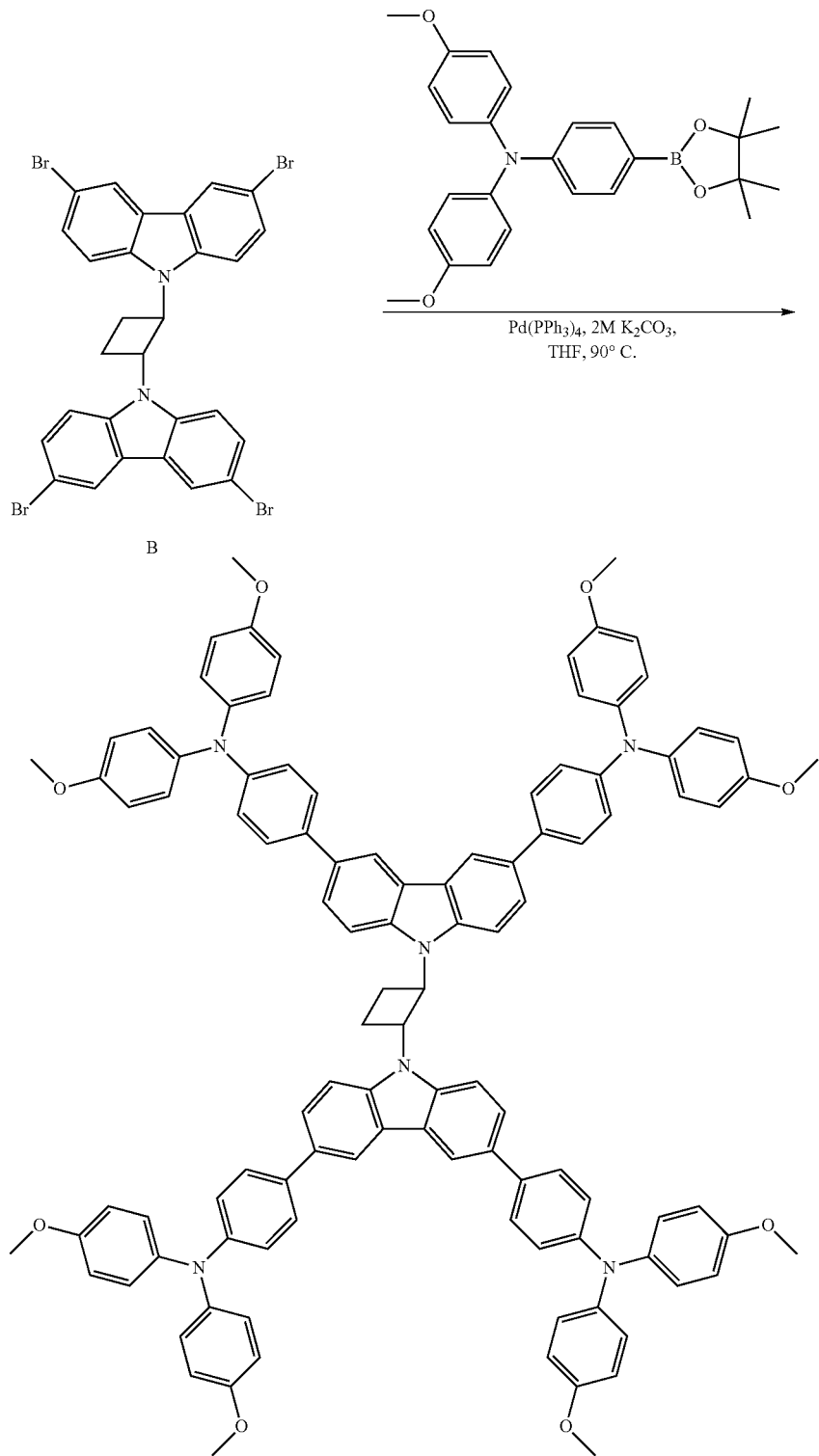

General Preparatory Scheme for Perovskite Solar Cells

As substrate for the devices, etched fluorine-doped tin oxide (FTO) is used and is cleaned prior to assembly. The cleaned FTO is then spin coated with a solution of SnO$_2$ and water then dried and briefly heated to 190° C. The remaining steps are performed under nitrogen conditions. A perovskite precursor solution is prepared using standard stock solutions in DMSO/DMF then spin coated onto the substrate. The resulting perovskite film is annealed at 100° C. Solutions of the hole transporting material are prepared with the hole transporting compound of interest, chlorobenzene, and any additives. HTM layers are applied to the perovskite films by spin coating techniques then gold electrodes are deposited by thermal evaporation. FIG. 1 shows a cross-sectional view of the resulting photovoltaic cell using the cyclobutyl-based hole transporting material of compound 5 (V1366).

EXAMPLES

Information on examples of real embodiments is provided below, describing the modes of preparation compounds (1-7) of the present invention and properties thereof. This information is provided for the illustrative purpose and is not limiting the scope of the present invention.

Synthesis of the Intermediates A and B 1,2-bis(9H-carbazol-9-yl)cyclobutane (A)

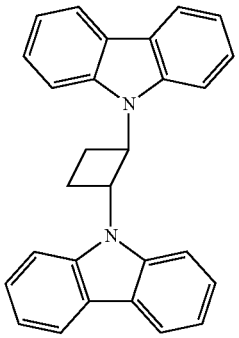 [SMILES: c1ccc2c(c1)c1ccccc1n2C1CCC1n1c2ccccc2c2ccccc21]

A solution of 9-vinylcarbazole (12 g, 62 mmol) in acetone (125 mL) was irradiated (GR.E. 125 W helios italquartz) for 15 hours at room temperature. Air was bubbled through the solution continuously. The precipitated product was filtered and recrystallized from acetone. The precipitated product was recovered as pale creamy crystals. (8.5 g, 70.8% yield).

$^1$H NMR (400 MHz, THF-d$_6$) δ 8.02 (d, J=8.0 Hz, 4H), 7.72 (d, J=8.0 Hz, 4H), 7.34 (t, J=7.6 Hz, 4H), 7.13 (t, J=7.6 Hz, 4H), 6.53-6.29 (m, 2H), 3.22-2.99 (m, 2H), 2.80-2.63 (m, 2H).

$^{13}$C NMR (101 MHz, THF) 138.27, 123.59, 121.69, 118.15, 117.15, 107.88, 52.48, 18.59.

1,2-bis(3,6-dibromo-9H-carbazol-9-yl)cyclobutane (B)

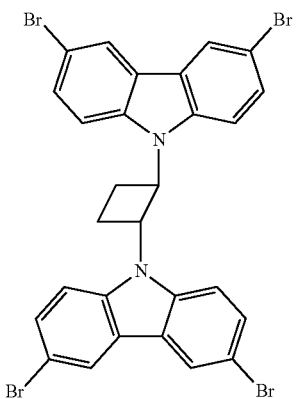 [SMILES: Brc1ccc2c(c1)c1cc(Br)ccc1n2C1CCC1n1c2ccc(Br)cc2c2cc(Br)ccc21]

Compound (A) (1.9 g, 4.9 mmol) was dissolved in THF (50 mL). Afterwards, 20% H$_2$SO$_4$ (50 mL) solution was added. Then KBr and KBrO$_3$ solution (69 mL H$_2$O, KBr 4.1 g, KBrO$_3$ 1.15 g) was slowly added dropwise 10 mL/min and stirred at room temperature for 72 hours. The precipitate was collected by filtration, washed with water, and then with hot methanol for three times. The precipitated product was recovered as white crystals of product B. (3.1 g, 88.6% yield).

$^1$H NMR (400 MHz, THF-d$_6$) δ 8.26 (s, 4H), 7.65 (d, J=8.8 Hz, 4H), 7.50 (d, J=8.8 Hz, 4H), 6.41-6.13 (m, 2H), 3.14-2.96 (m, 2H), 2.85-2.64 (m, 2H).

$^{13}$C NMR (101 MHz, THF) δ 139.05, 129.02, 124.33, 123.45, 112.47, 111.59, 54.51, 20.75.

Example 1

1,2-bis[3,6-bis(4,4'-dimethoxy)diphenylamino-9H-carbazol-9-yl]cyclobutane (see Scheme 1, compound 1 or V1244)

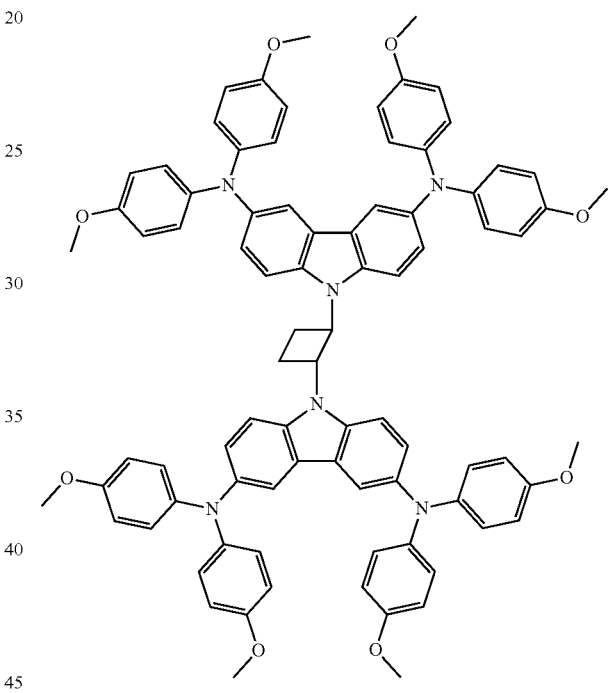

A solution of intermediate B (0.5 g, 0.7 mmol, 1 eq) and 4,4'-dimethoxydiphenylamine (0.98 g, 4.3 mmol, 6 eq) in anhydrous toluene (7 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added and the solution was refluxed under argon atmosphere for 5 hours. After cooling to room temperature, the reaction mixture was filtered through celite, extracted with ethylacetate and distilled water. The organic layer was dried over anhydrous Na$_2$SO$_4$, filtered, and the solvent evaporated. The crude product was purified by column chromatography using 3:9.5 v/v THF/n-hexane as an eluent. The obtained product was precipitated from acetone into 15 times excess of ethanol. The precipitate was filtered off and washed with ethanol to collect the product, V1244. The precipitated product was recovered as a pale green solid. (0.52 g, 56.3% yield).

$^1$H NMR (400 MHz, THF-d$_6$) δ 7.66-7.51 (m, 8H), 7.08 (d, J=8.8, 1.7 Hz, 4H), 6.88 (d, J=8.8 Hz, 16H), 6.71 (d, J=8.8 Hz, 16H), 6.34-6.18 (m, 2H), 3.69 (s, 24H), 3.03-2.91 (m, 2H), 2.70-2.60 (m, 2H).

$^{13}$C NMR (101 MHz, THF) δ 154.95, 142.47, 141.24, 137.03, 124.27, 124.13, 123.92, 116.39, 114.17, 110.55, 54.75, 54.54, 20.62.

Elemental analysis: Calculated, %: C, 77.88; H, 5.76; N, 6.49. $C_{84}H_{74}N_6O_8$. Found, %: C, 77.97; H, 5.72; N, 6.41.

Example 2

1,2-Bis[3,6-bis(4,4'-dimethyl)diphenylamino-9H-carbazol-9-yl]cyclobutane (V1296) (see Scheme 1, Compound 2 or V1296)

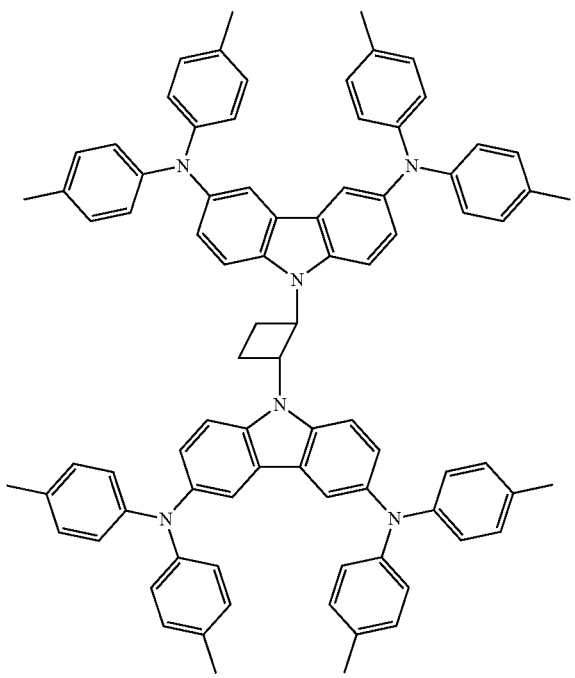

A solution of intermediate B (0.5 g, 0.7 mmol, 1 eq) and 4,4'-dimethyldiphenylamine (0.84 g, 4.3 mmol, 6 eq) in anhydrous toluene (7 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added and the solution was refluxed under argon atmosphere for 22 hours. After cooling to room temperature, reaction mixture was filtered through celite, extracted with ethylacetate and distilled water. The organic layer was dried over anhydrous $Na_2SO_4$, filtered, and the solvent evaporated. The crude product was recrystallized from ethanol/toluene 1:1 gave as pale green crystals of V1296 (0.46 g, 55.4% yield). $^1$H NMR (400 MHz, THF-$d_6$) δ 7.67 (s, 4H), 7.66 (d, J=8.8 Hz, 4H), 7.12 (d, J=8.8 Hz, 4H), 6.93 (d, J=8.4 Hz, 16H), 6.85 (d, J=8.4 Hz, 16H), 6.39-6.25 (m, 2H), 3.09-2.92 (m, 2H), 2.79-2.59 (m, 2H), 2.22 (s, 24H).

$^{13}$C NMR (101 MHz, THF) δ 144.59, 138.67, 135.70, 128.59, 127.45, 123.16, 122.52, 120.71, 116.07, 108.91, 52.89, 18.84, 17.92.

Elemental analysis: Calculated, %: C, 86.41; H, 6.39; N, 7.20. $C_{84}H_{74}N_6$. Found, %: C, 86.24; H, 6.45; N, 7.31.

Example 3

1,2-bis(3,6-bisdiphenylamino-9H-carbazol-9-yl)cyclobutane (see Scheme 1, Compound 3 or V1297)

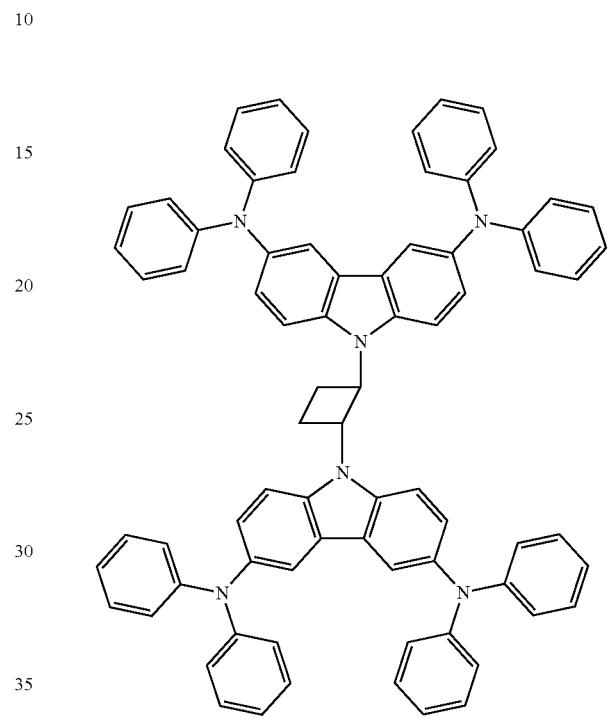

A solution of intermediate B (0.5 g, 0.7 mmol, 1 eq) and diphenylamine (0.72 g, 4.3 mmol, 6 eq) in anhydrous toluene (7 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added and the solution was refluxed under argon atmosphere for 27 hours. After cooling to room temperature, the reaction mixture was filtered through celite, extracted with ethylacetate and distilled water. The organic layer was dried over anhydrous $Na_2SO_4$, filtered and solvent evaporated. The crude product was purified by column chromatography using 1:9 v/v THF/n-hexane as an eluent. The obtained product was precipitated from THF into 15 times excess of n-hexane. The precipitate was filtered off and washed with hexane to collect the product, V1297. The precipitated product was recovered as a pale green solid. (0.44 g, 58.7% yield).

$^1$H NMR (400 MHz, DMSO-$d_6$) δ 7.89 (d, J=9.2 Hz, 4H), 7.83 (d, J=2.0 Hz, 4H), 7.27-7.05 (m, 20H), 6.97-6.79 (m, 24H), 6.39-6.24 (m, 2H), 2.93-2.75 (m, 2H), 2.70-2.55 (m, 2H).

$^{13}$C NMR (101 MHz, DMSO) δ 148.42, 139.76, 138.02, 129.65, 126.33, 124.09, 122.46, 122.02, 119.67, 112.27, 54.24, 21.65.

Elemental analysis: Calculated, %: C, 86.50; H, 5.54; N, 7.96. $C_{76}H_{58}N_6$. Found, %: C, 86.65; H, 5.50; N, 7.85.

Example 4

1,2-bis{3,6-bis[N-(9,9-dimethylfluoren-2-yl)-N-(4-methoxyfenil)amino]-9H-carbazol-9-yl}cyclobutane (Compound 4 or V1361)

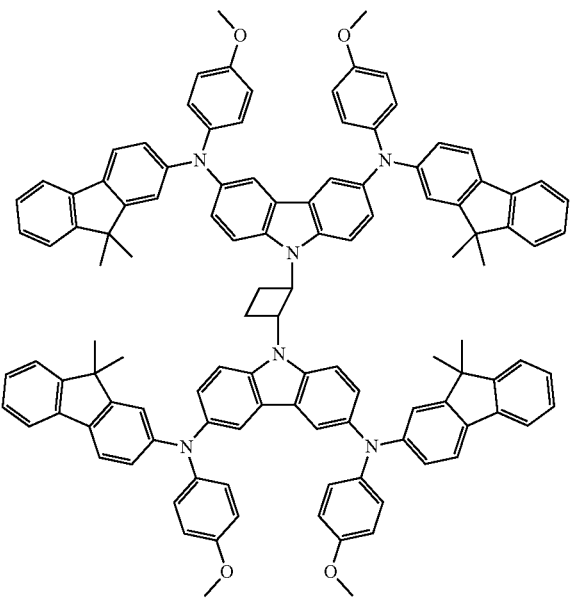 [SMILES: COc1ccc(N(c2ccc3c(c2)C(C)(C)c2ccccc2-3)c2ccc3c(c2)c2cc(N(c4ccc(OC)cc4)c4ccc5c(c4)C(C)(C)c4ccccc4-5)ccc2n3C2CCC2n2c3ccc(N(c4ccc(OC)cc4)c4ccc5c(c4)C(C)(C)c4ccccc4-5)cc3c3cc(N(c4ccc(OC)cc4)c4ccc5c(c4)C(C)(C)c4ccccc4-5)ccc32)cc1]

A solution of intermediate B (0.5 g, 0.7 mmol, 1 eq) and N-(4-methoxyphenyl)-9,9-dimethyl-9H-fluoren-2-amine (1.35 g, 4.3 mmol, 6 eq) in anhydrous toluene (10 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added, and the solution was refluxed under argon atmosphere for 5 hours. After cooling to room temperature, reaction mixture was filtered through celite, extracted with ethylacetate and distilled water. The organic layer was dried over anhydrous $Na_2SO_4$, filtered, and the solvent evaporated. The crude product was purified by column chromatography using 5.5:19.5 v/v THF/n-hexane as an eluent. The obtained product was precipitated from THF into 15 times excess of n-hexane. The precipitate was filtered off and washed with hexane to collect V1361 as a yellow-green solid. (0.67 g, 57.3% yield).

$^1$H NMR (400 MHz, DMSO-$d_6$) δ 7.88 (d, J=8.4 Hz, 4H), 7.78 (s, 4H), 7.55 (d, J=7.8 Hz, 4H), 7.49 (d, J=7.8 Hz, 4H), 7.28 (d, J=7.2 Hz, 4H), 7.24-7.16 (m, 8H), 7.11 (t, J=7.4 Hz, 4H), 7.00 (d, J=8.6 Hz, 8H), 6.93 (s, 4H), 6.80 (d, J=8.6 Hz, 8H), 6.69 (d, J=8.4 Hz, 4H), 6.42-6.23 (m, 2H), 3.64 (s, 12H), 2.92-2.77 (m, 2H), 2.76-2.56 (m, 2H), 1.17 (s, 24H).

$^{13}$C NMR (101 MHz, DMSO) δ 155.83, 154.82, 153.15, 149.03, 141.15, 140.42, 139.09, 137.50, 131.40, 127.37, 126.76, 126.35, 125.32, 123.94, 122.86, 121.12, 119.41, 119.19, 118.17, 115.27, 114.25, 111.87, 55.55, 53.96, 46.56, 27.29, 27.25.

Elemental analysis: Calculated, %: C, 84.95; H, 6.02; N, 5.12. $C_{116}H_{98}N_6O_2$. Found, %: C, 84.85; H, 6.06; N, 5.15.

Example 5

1,2-bis{3,6-bis[N-(9-ethylcarbazol-3-yl)-N-(4-methoxyfenil)amino]-9H-carbazol-9-yl}cyclobutane (Compound 5 or V1366)

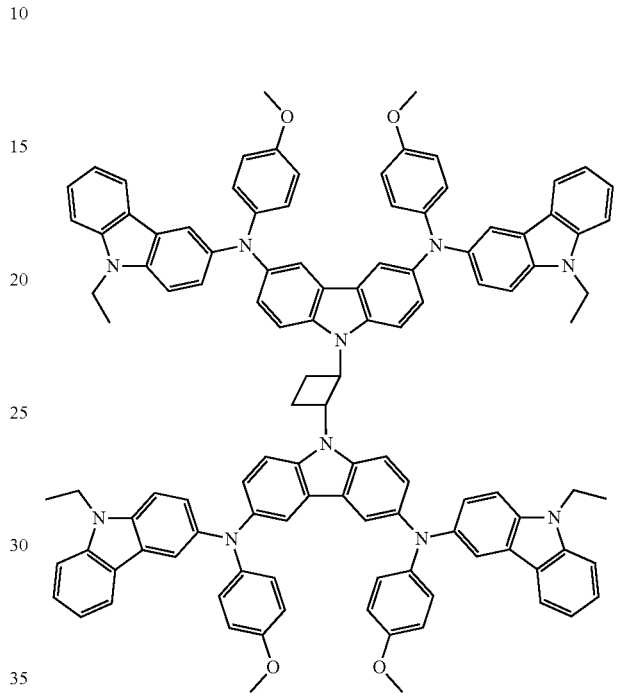

A solution of intermediate B (0.5 g, 0.7 mmol, 1 eq) and 9-ethyl-N-(4-methoxyphenyl)-9H-carbazol-3-amine (1.35 g, 4.3 mmol, 6 eq) in anhydrous toluene (10 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added, and the solution was refluxed under argon atmosphere for 5 hours. After cooling to room temperature, reaction mixture was filtered through celite, extracted with ethylacetate and distilled water. The organic layer was dried over anhydrous $Na_2SO_4$, filtered, and the solvent evaporated. The crude product was purified by column chromatography using 4.5:8 v/v THF/n-hexane as an eluent. The obtained product was precipitated from THF into 15 times excess of n-hexane. The precipitate was filtered off and washed with hexane to collect V1366 as a yellow-green solid. (0.71 g, 60.7% yield).

$^1$H NMR (400 MHz, THF-$d_6$) δ 7.84 (d, J=8.0 Hz, 4H), 7.75 (s, 4H), 7.69-7.58 (m, 8H), 7.37 (d, J=8.4 Hz, 4H), 7.33-7.25 (m, 8H), 7.19-7.11 (m, 8H), 6.97 (t, J=7.4 Hz, 4H), 6.92 (d, J=8.8 Hz, 8H), 6.68 (d, J=8.8 Hz, 8H), 6.38-6.26 (m, 2H), 4.31 (q, J=7.0 Hz, 8H), 3.65 (s, 12H), 3.08-2.93 (m, 2H), 2.71-2.58 (m, 2H), 1.33 (t, J=7.0 Hz, 12H).

$^{13}$C NMR (101 MHz, THF) δ 154.55, 143.30, 141.94, 141.50, 140.44, 136.86, 136.20, 125.19, 124.98, 124.35, 123.79, 123.69, 123.56, 122.77, 120.21, 118.13, 116.09, 115.97, 114.11, 110.49, 108.88, 108.19, 54.74, 54.52, 37.04, 20.57, 13.14.

Elemental analysis: Calculated, %: C, 81.82; H, 5.76; N, 8.52. $C_{112}H_{94}N_{10}O_4$. Found, %: C, 81.91; H, 5.70; N, 7.50.

Example 6

1,2-bis{3,6-bis[N,N-bis(9-ethylcarbazol-3-yl)amino]-9H-carbazol-9-yl}cyclobutane (Compound 6 or V1367)

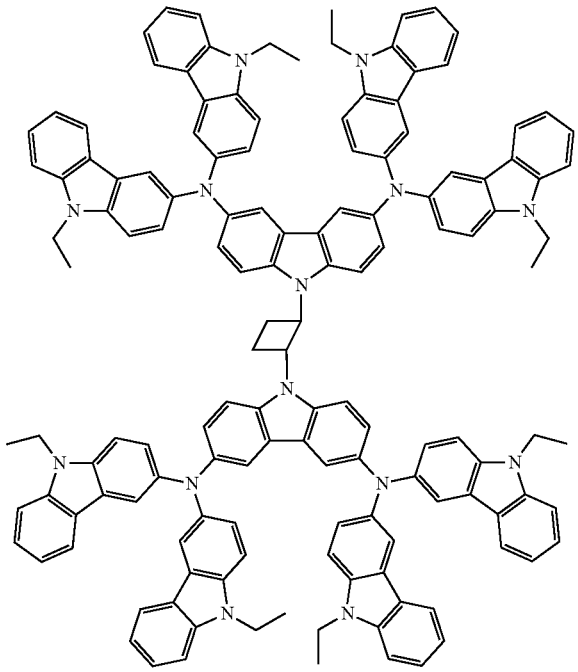 [SMILES: CCn1c2ccccc2c2cc(N(c3ccc4c(c3)c3ccccc3n4CC)c3ccc4c(c3)c3cc(N(c5ccc6c(c5)c5ccccc5n6CC)c5ccc6c(c5)c5ccccc5n6CC)ccc3n4C3CCC3n3c4ccc(N(c5ccc6c(c5)c5ccccc5n6CC)c5ccc6c(c5)c5ccccc5n6CC)cc4c4cc(N(c5ccc6c(c5)c5ccccc5n6CC)c5ccc6c(c5)c5ccccc5n6CC)ccc43)ccc21]

A solution of intermediate B (0.5 g, 0.7 mmol, 1 eq) and bis(9-ethyl-9H-carbazol-3-yl)amine (1.72 g, 4.3 mmol, 6 eq) in anhydrous toluene (12 mL) was purged with argon for 30 minutes. Afterwards, palladium (II) acetate (0.02 eq), tri-tert-butylphosphonium tetrafluoroborate (0.027 eq) and sodium tert-butoxide (6 eq) were added, and the solution was refluxed under argon atmosphere for 6 hours. After cooling to room temperature, reaction mixture was filtered through celite, extracted with ethylacetate and distilled water. The resulting solid precipitate from extraction was filtered. The crude product was purified by column chromatography using 4.5:8 v/v THF/n-hexane as an eluent. The obtained product was precipitated from THF into 15 times excess of ethanol. The precipitate was filtered off and washed with ethanol to collect V1367 as a yellow-green solid. (0.62 g, 43.7% yield).

$^1$H NMR (400 MHz, THF-$d_6$) δ 7.92-7.50 (m, 24H), 7.38-7.10 (m, 36H), 6.93 (t, J=7.4 Hz, 8H), 6.46-6.29 (m, 2H), 4.24 (q, J=6.8 Hz, 16H), 3.11-2.94 (m, 2H), 2.70-2.57 (m, 2H), 1.28 (t, J=6.8 Hz, 24H).

$^{13}$C NMR (101 MHz, THF) δ 142.76, 142.40, 140.41, 136.70, 135.94, 128.72, 127.96, 125.07, 124.46, 123.66, 123.32, 122.85, 120.24, 118.04, 115.74, 115.44, 110.45, 108.83, 108.10, 54.73, 37.01, 13.17.

Elemental analysis: Calculated, %: C, 84.39; H, 5.77; N, 9.84. $C_{140}H_{114}N_{14}$. Found, %: C, 84.28; H, 5.83; N, 9.89.

Example 7

1,2-bis|3,6-bis{4-[N,N-bis(4-methoxyfenil)amino]fenil}-9H-carbazol-9-yl|cyclobutane (see Scheme 2, Compound 7 or V1321)

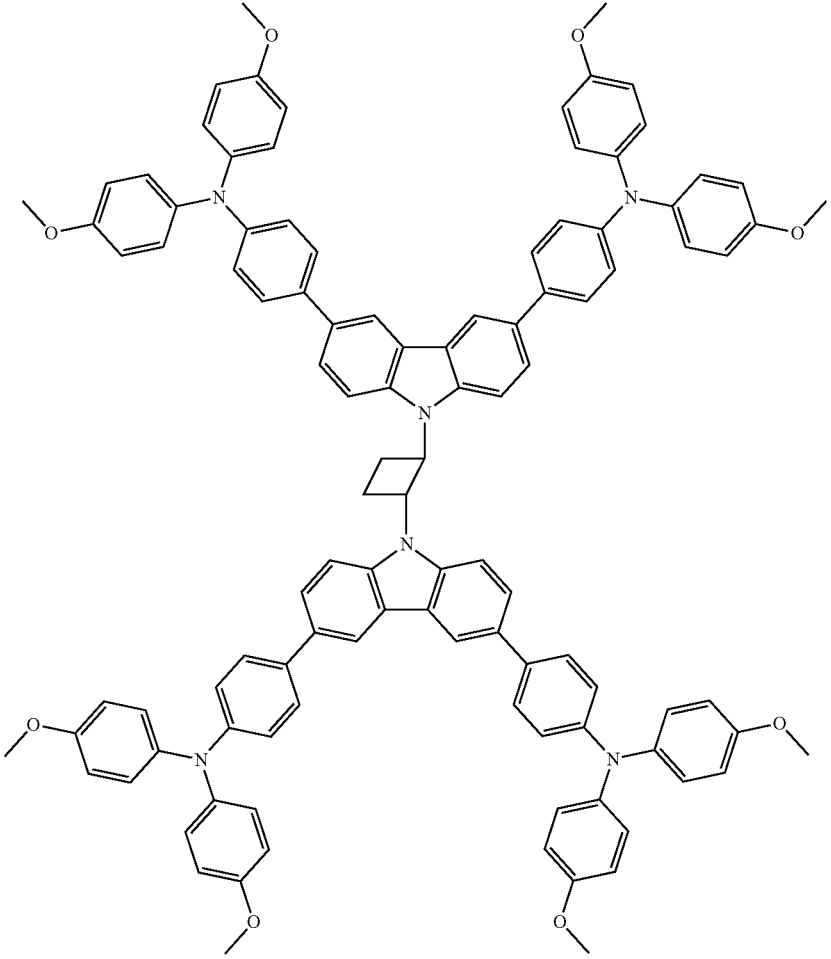

A solution of intermediate B (0.1 g, 0.14 mmol, 1 eq) and 4-methoxy-N-(4-methoxyphenyl)-N-(4-(4,4,5,5-tetramethyl-1,3,2-dioxaborolan-2-yl)phenyl)aniline (0.61 g, 1.4 mmol, 10 eq) in anhydrous THF (10 mL) was purged with argon for 10 minutes. Afterwards, tetrakis(triphenylphosphine)palladium(0) (0.115 eq) and 2M $K_2CO_3$ (4 mL) were added, and the solution was heated for 3 hours at 90° C. After cooling to room temperature, reaction mixture was filtered through celite, extracted with ethylacetate and distilled water. The organic layer was dried over anhydrous $Na_2SO_4$, filtered, and the solvent evaporated. The crude product was purified by column chromatography using 4:8.5 v/v THF/n-hexane as an eluent. The obtained product was precipitated from THF into 15 times excess of n-hexane. The precipitate was filtered off and washed with hexane to collect V1321 as a pale yellow-green solid. (0.1 g, 43.9% yield).

$^1$H NMR (400 MHz, THF-$d_6$) δ 8.34 (s, 4H), 7.76 (d, J=8.8 Hz, 4H), 7.59 (d, J=8.8 Hz, 4H), 7.51 (d, J=8.6 Hz, 8H), 7.02 (d, J=8.8 Hz, 16H), 6.97 (d, J=8.6 Hz, 8H), 6.82 (d, J=8.8 Hz, 16H), 6.50-6.35 (m, 2H), 3.74 (s, 24H), 3.19-3.02 (m, 2H), 2.86-2.68 (m, 2H).

$^{13}$C NMR (101 MHz, THF) δ 154.17, 145.70, 139.26, 137.80, 132.26, 130.62, 125.34, 124.20, 122.65, 122.48, 119.37, 115.94, 112.55, 108.21, 52.85, 52.74, 18.86.

Elemental analysis: Calculated, %: C, 81.08; H, 5.67; N, 5.25. $C_{108}H_{90}N_6O_8$. Found, %: C, 81.35; H, 5.54; N, 5.23.

Example 8

Ionization Potential Measurements

The solid-state ionization potential (Ip) of the layers of the compounds of formulae (1) to (7) was measured by the electron photoemission in air method (E. Miyamoto, Y. Yamaguchi, M. Masaaki, Electrophotography, 1989, vol. 28, pp. 364). The samples for the ionization potential measurement were prepared by dissolving materials in THF and were coated on Al plates pre-coated with ~0.5 μm thick methylmethacrylate and methacrylic acid copolymer adhesive layer. The thickness of the transporting material layer was $0.5^{-1}$ μm. Photoemission experiments are carried out in vacuum, and high vacuum is one of the main requirements for these measurements. If vacuum is not high enough the sample surface oxidation and gas adsorption influence the measurement results. In our case, however, the organic materials investigated are stable enough to oxygen, and the measurements may be carried out in the air. The samples were illuminated with monochromatic light from the quartz monochromator with deuterium lamp. The power of the incident light beam was $(2-5)\cdot 10^{-8}$ W. The negative voltage of −300 V was supplied to the sample substrate. The counter-electrode with the 4.5×15 mm$^2$ slit for illumination was placed at 8 mm distance from the sample surface. The counter-electrode was connected to the input of the BK2-16 type electrometer, working in the open input regime for the photocurrent measurement. A $10^{-15}$-$10^{-12}$ A strong photocurrent was flowing in the circuit under illumination. The photocurrent I is strongly dependent on the incident light photon energy h. The $I^{0.5}$=f(hv) dependence was plotted. Usually the dependence of the photocurrent on incident light quanta energy is well described by linear relationship between $I^{0.5}$ and hv near the threshold. The linear part of this dependence was extrapolated to the hv axis and $I_p$ value was determined as the photon energy at the interception point. The $I_p$ results are presented in Table 1.

Example 9

Hole Drift Mobility Measurements

The samples for the hole mobility measurements were prepared by spin-coating the THF solutions of the synthesized compounds 1-7 or compositions of synthesized compounds with bisphenol-Z polycarbonate (PC-Z) (Iupilon Z-200 from Mitsubishi Gas Chemical Co.) in weight ratio 1:1 on the polyester films with conductive Al layer. THF was used for 1-7 compounds. The layer thickness was in the range of 5-10 μm. The hole drift mobility was measured by xerographic time of flight technique (XTOF) (Vaezi-Nejad, S. M., It. J. Electronics, 1987, 62, No 3, 361-384). Electric field was created by positive corona charging. The charge carriers were generated at the layer surface by illumination with pulses of nitrogen laser (pulse duration was 2 ns, wavelength 337 nm). The layer surface potential decrease as a result of pulse illumination was up to 1-5% of initial potential before illumination. The capacitance probe that was connected to the wide frequency band electrometer measured the speed of the surface potential decrease dU/dt. The transit time $t_t$ was determined by the kink on the curve of the dU/dt transient in double logarithmic scale. The drift mobility was calculated by the formula $\mu=d^2/U_0 t_t$, where d is the layer thickness, $U_0$—the surface potential at the moment of illumination. The μ results are presented in Table 1.

TABLE 1

Ionization potential ($I_p$) and charge mobility values ($\mu$) of the hole transporting compounds 1-7 and Spiro-OMeTAD

| No. | Formula | $I_p$, eV | Mobility $\mu_0$, cm$^2$V$^{-1}$s$^{-1}$ (at 0 V/cm) | Mobility, cm$^2$V$^{-1}$s$^{-1}$ (at 6.4·10$^5$ V/cm) |
| --- | --- | --- | --- | --- |
| 1 or V1244 | | 5.03 | 7.9 × 10$^{-6}$ | 9.2 × 10$^{-4}$ |
| 2 or V1296 | | 5.46 | 1.7 × 10$^{-4}$ | 4.7 × 10$^{-4}$ |

TABLE 1-continued

Ionization potential ($I_p$) and charge mobility values ($\mu$) of the hole transporting compounds 1-7 and Spiro-OMeTAD

| No. | Formula | $I_p$, eV | Mobility $\mu_0$, cm$^2$V$^{-1}$s$^{-1}$ (at 0 V/cm) | Mobility, cm$^2$V$^{-1}$s$^{-1}$ (at 6.4·10$^5$ V/cm) |
|---|---|---|---|---|
| 3 or V1297 | | 5.48 | 3.3 × 10$^{-7}$ | 1.2 × 10$^{-4}$ |
| 4 or V1361 | | 5.28 | 2.5 × 10$^{-5}$<br>3 × 10$^{-7}$<br>(PC-Z, 1:1) | 2.5 × 10$^{-3}$<br>2.6 × 10$^{-4}$<br>(PC-Z, 1:1) |

TABLE 1-continued

Ionization potential ($I_p$) and charge mobility values ($\mu$) of the hole transporting compounds 1-7 and Spiro-OMeTAD

| No. | Formula | $I_p$, eV | Mobility $\mu_0$, cm$^2$V$^{-1}$s$^{-1}$ (at 0 V/cm) | Mobility, cm$^2$V$^{-1}$s$^{-1}$ (at 6.4·10$^5$ V/cm) |
|---|---|---|---|---|
| 5 or V1366 | [structure] | 4.77 | $3.5 \times 10^{-5}$ $3.4 \times 10^{-7}$ (PC-Z, 1:1) | $2.2 \times 10^{-3}$ $2.2 \times 10^{-5}$ (PC-Z, 1:1) |
| 6 or V1367 | [structure] | 4.78 | $2.5 \times 10^{-6}$ (PC-Z, 1:1) | $5.5 \times 10^{-5}$ (PC-Z, 1:1) |

TABLE 1-continued

Ionization potential ($I_p$) and charge mobility values ($\mu$) of the hole transporting compounds 1-7 and Spiro-OMeTAD

| No. | Formula | $I_p$, eV | Mobility $\mu_0$, cm$^2$V$^{-1}$s$^{-1}$ (at 0 V/cm) | Mobility, cm$^2$V$^{-1}$s$^{-1}$ (at $6.4 \cdot 10^5$ V/cm) |
|---|---|---|---|---|
| 7 or V1321 | 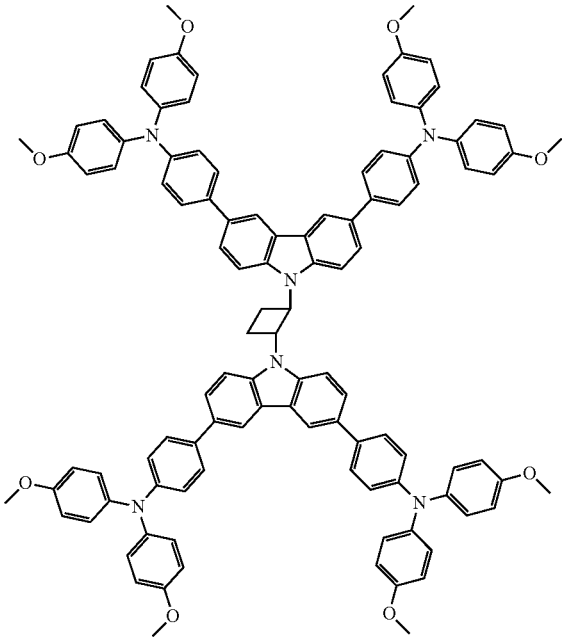 | 5.34 | $1 \times 10^{-5}$ | $2.3 \times 10^{-3}$ |
| Spiro-OMeTAD | 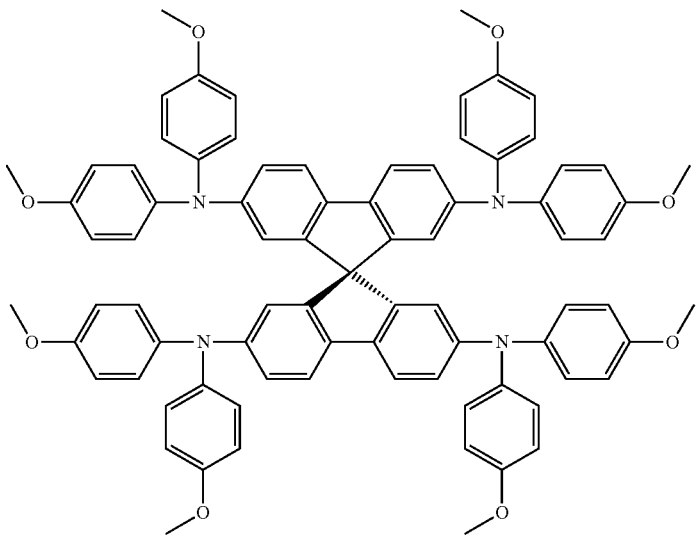 | 5.00 | $4.1 \cdot 10^{-5}$ | $5 \cdot 10^{-4}$ |

The estimated $I_p$ values of synthesized compounds 1, 5, and 6 are in range 4.77 eV-5.03 eV and are closed to the value of Spiro-OMeTAD (5.0 eV). Meanwhile, the $I_p$ values for compounds 2-4 and 7 are slightly higher, in range 5.28-5.48 eV. The measured charge mobility values of synthesized compounds 1, and 3-7 are also comparable to the values measured for Spiro-OMeTAD, while charge mobility of the compound 2 increase by c.a. one order of magnitude ($\mu_0=10^{-4}$ cm$^2$ V$^{-1}$ S$^{-1}$) at weak electric fields.

Example 10

Photovoltaic Cell Manufacture and Performance Measurements

The performance of hole transporter compounds 1-7 were tested in mixed perovskite-based solar cells using a mesoporous TiO$_2$ photo-anode and an Au cathode (FTO/compact TiO$_2$/mesoporous compact TiO$_2$/mixed perovskite/ V1244/Au).

The preparation of Perovskite solar cells was as follows. Chemically etched FTO glass (Nippon Sheet Glass) was cleaned with detergent solution, acetone, and isopropanol. The substrate was spin coated with a thin layer of $SnO_2$ nanoparticle film at 3000 rpm for 30 s with a ramp-up of 1500 rpm·s$^{-1}$ from a commercially available solution in water; the weight ratio of $SnO_2$ solution to water is 1:3. After spin coating, the substrate was immediately dried on a hotplate at 80° C., and the substrates were then heated at 190° C. for 30 min. After cooling, 1.5 M $(FAPbI_3)_{0.85}(MAPbBr_3)_{0.15}$ perovskite precursor solution was prepared by mixing of $PbI_2$, $PbBr_2$, MABr and FAI in DMSO/DMF mixed solvent (1/8). And then, perovskite solutions are successively spin-coated on the substrates at 1000 rpm for 10 s and 5000 rpm for 30 s, respectively. 1 ml of di-ether was dropped in 10 s at 5000 rpm. Perovskite films were annealed at 100° C. for 40 min. The reference solution was prepared by dissolving 91 mg of Spiro-OMeTAD (Merck) with additives in 1 mL of chlorobenzene. As additives, 21 μL of Li-bis(trifluoromethanesulfonyl) imide from the stock solution (520 mg in 1 mL of acetonitrile), 16 μL of FK209 [tris(2-(1H-pyrazol-1-yl)-4-tert-butylpyridine)-cobalt(III) tris(bis trifluoromethylsulfonyl)imide) (375 mg in 1 mL of acetonitrile) and 36 μL of 4-tertbutylpyridine were added. Solutions of the cyclobutyl-based hole transporting compounds 1-7 were prepared by dissolving synthesized compounds at the optimized concentration of 40 mM with additives in 1 mL of chlorobenzene. As additives, 15 μL of Li-bis(trifluoromethanesulfonyl) imide from the stock solution, 10 μL of FK209 and 26 μL of 4-tertbutylpyridine were added. The HTM layers were formed by spin-coating the solution at 4000 rpm for 20 s and followed by the deposition of the 70 nm thick Au electrode by a thermal evaporation. All the preparative work to deposit perovskite and HTMs was done inside the glove box filled with nitrogen to minimize the influence of moisture.

Current-voltage characteristics were recorded by applying an external potential bias to the cell while recording the generated photocurrent with a digital source meter (Keithley Model 2400). The light source was a 450 W xenon lamp (Oriel) equipped with a SchottK113 Tempax sunlight filter (Praezisions Glas & Optik GmbH) to match the emission spectrum of the lamp to the AM1.5G standard. Before each measurement, the exact light intensity was determined using a calibrated Si reference diode equipped with an infrared cutoff filter (KG-3, Schott). The voltage scan rate was 100 mV·s$^{-1}$ and no device preconditioning such as light soaking or forward voltage bias applied for long time, was applied before starting the measurement. The cells were masked with the active area of 0.891 cm$^2$ to fix the active area and reduce the influence of the scattered light for the small device.

Figure 2:
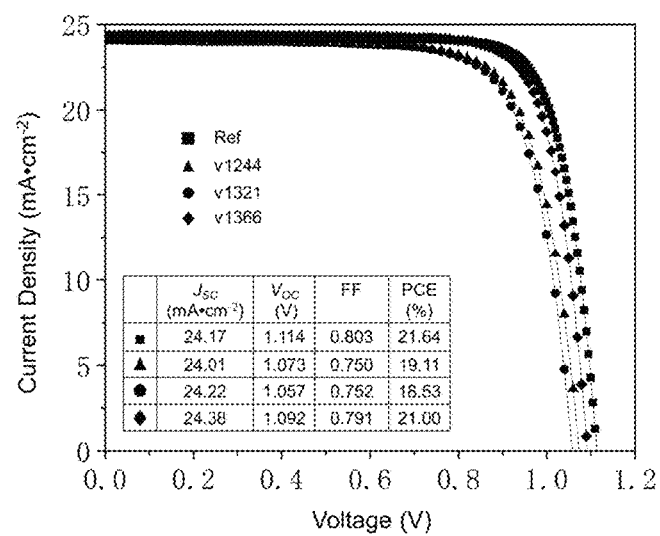
FIG. 2 shows the Current-Voltage curve of photovoltaic cells where compounds 1, 5, and 7 corresponding to compounds V1244, V1366, and V1321 and Spiro-OMeTAD are explored as hole transporting materials.
Figure 3:
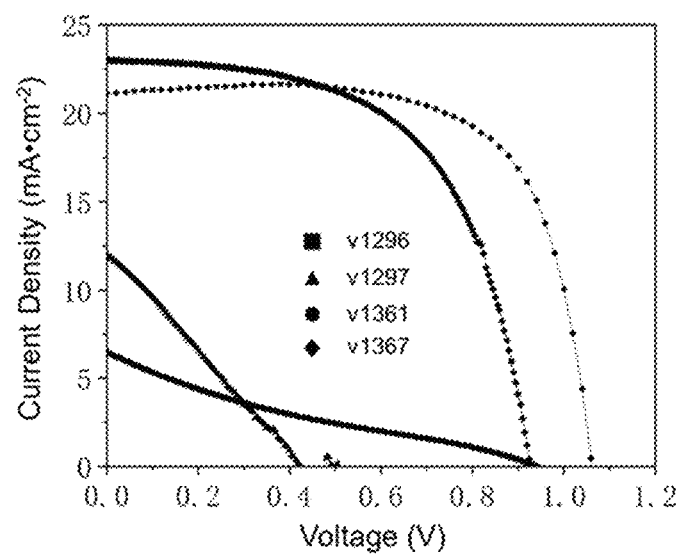
FIG. 3 shows the Current-Voltage curve of photovoltaic cells where compounds 2, 3, 4 and 6 corresponding to compounds V1296, V1297, V1361, and V1367 are explored as hole transporting materials.

Results of the performance characterization are shown in Table 2. FIG. 2 shows the typical current density-voltage (J-V) curves (reverse scan) for the PSCs with spiro-OMeTAD as a reference, compound 1 (V1244), compound 7 (V1321), and compound 5 (V1366), respectively. Devices having cyclobutyl-based HTMs exhibit photoelectric conversion performance comparable to spiro-OMeTAD, especially for compound 5 (V1366), which showed even higher photocurrent. However, the devices with compounds 2 (V1296), 3 (V1297), 4 (V1361), and 6 (V1367) as the cyclobutyl-based HTMs exhibit relatively low PCE (FIG. 3). Such deteriorated performance of compound 2 (V1296) and compound 3 (V1297) could be explained by quite deep HOMO levels, which could lead to the mismatch with the perovskite valence band, while compound 6 (V1367) has one of the lowest hole drift mobility among the series. On the other hand, the PCE of 21% consisting of JSC of 24.38 mA·cm-2, an open-circuit voltage of 1.092 V, and an FF of 79.1% was achieved for the compound 5 (V1366)-based device in comparison to 21.64% for the spiro-OMeTAD with $J_{SC}$ of 24.17 mA·cm-2, a $V_{OC}$ of 1.114 V, and an FF of 80.3%, showing that molecular engineering of side-arms fully dictates the performance of the final device.

TABLE 2

Photovoltaic cell performance compounds 1-7 and Spiro-OMeTAD

| No. | $J_{SC}$ (mA · cm$^{-2}$) | $V_{oc}$ (V) | FF | PCE (%) |
|---|---|---|---|---|
| 1 or V1244 | 24.01 | 1.073 | 0.750 | 19.11 |
| 2 or V1296 | 6.49 | 0.942 | 0.198 | 1.21 |
| 3 or V1297 | 12.00 | 0.506 | 0.217 | 1.32 |
| 4 or V1361 | 21.11 | 1.061 | 0.693 | 15.26 |
| 5 or V1366 | 24.38 | 1.092 | 0.791 | 21.00 |
| 6 or V1367 | 22.99 | 0.927 | 0.584 | 12.44 |
| 7 or V1321 | 24.22 | 1.057 | 0.752 | 18.53 |
| Spiro-OMeTAD | 24.17 | 1.114 | 0.803 | 21.64 |

Example 11

Perovskite Solar Cell Module Manufacture and Performance Measurements

The performance of hole transporter compounds 5 (V1366) as an HTM in a perovskite solar cell module was compared to a module using a standard HTM, Spiro-OMeTAD.

The module composed of eight-strip cells connected in series was scribed using a YAG laser from Newport. For fabrication of solar modules, 6.5 cm×7 cm FTO substrates were patterned by a laser with a power of 1500 mW and a scribing width of 80 μm. The substrate was spin coated with a thin layer of $SnO_2$ nanoparticle film at 3000 rpm for 30 s with a ramp-up of 1500 rpm·s-1 from a commercially available solution in water; the weight ratio of $SnO_2$ solution to water is 1:3. After spin coating, the substrate was immediately dried on a hotplate at 80° C., and the substrates were then heated at 190° C. for 30 min. After cooling, 1 M (FAPbI3)0.85(MAPbBr3)0.15 perovskite precursor solution was prepared by mixing of PbI2, PbBr2, MABr and FAI in DMSO/DMF mixed solvent (1/4). And then, perovskite solutions are successively spin-coated on the substrates at 1000 rpm for 10 s and 4000 rpm for 30 s, respectively. 600 μL of chlorobenzene was dropped in 10 s at 4000 rpm. Perovskite films were annealed at 100° C. for 40 min. A solution of compound 5 (V1366) HTM was prepared by dissolving 40 mM of V1366 with additives in 1 mL of chlorobenzene. As additives, 15 μL of Li-bis(trifluoromethanesulfonyl) imide from the stock solution, 10 μL of FK209 and 26 μL of 4-tertbutylpyridine were added. The HTM layer was formed by spin-coating the solution at 4000 rpm for 30 s and followed by the deposition of the 70 nm thick Au electrode by a thermal evaporation. Next, $SnO_2$/Perovskite/HTM layers were scribed by a laser with a power of 1000 mW and a scribing width of 500 μm. Finally, a gold electrode was deposited by thermal evaporation, and gold layers were scribed by a laser with a power of 1000 mW and a scribing width of 100 μm.

Characterization of the modules was carried out similarly to the photovoltaic cells with the following modifications. The active area of each module was counted by using Nano Measurer 1.2. IPCE spectra were recorded as functions of wavelength under a constant white light bias of ≈10 mW cm$^{-2}$ supplied by an array of white light emitting diodes. The excitation beam coming from a 300 W xenon lamp (ILC Technology) was focused through a Gemini-180 double monochromator (Jobin Yvon Ltd) and chopped at ≈2 Hz. The signal was recorded using a Model SR830 DSP Lock-In Amplifier (Stanford Research Systems). All measurements were characterized at room temperature in air.

To characterize the upscaling performance of the cyclobutyl-based HTM, we fabricated compound 5 (V1366)-based perovskite modules sized of 6.5×7 cm. The module exhibited a PCE of 19.06% with $J_{SC}$ of 2.99 mA·cm$^{-2}$, a $V_{OC}$ of 8.275 V, and an FF of 77%. To the best of our knowledge, the PCE value over 19% is the highest PCE ever reported for non-spiro-OMeTAD based perovskite module.

REFERENCES

1. Y. Rong, Y. Hu, A. Mei, H. Tan, M. I. Saidaminov, S. II. Seok, M. D. McGehee, E. H. Sargent. E. H.; Han, H. Science 2018, 361, No. eaat8235.1
2. A. Kojima, K. Teshima, Y. Shirai, T. Miyasaka. J. Am. Chem. Soc. 2009, 131, 6050-6051.
3. Y. Shi, K. Hou, Y. Wang, K. Wang, H. C. Ren, M. Y. Pang, F. Chen, S. Zhang. J. Mater. Chem. A, 2016, 4, 5415-5422.
4. T. P. I. Saragi, T. Spehr, A. Siebert, T. Fuhrmann-Lieker, J. Salbeck, Chem. Rev., 2007, 107, 1011-1065.
5. H. Jiang, J. Sun, J. Zhang, Curr. Org. Chem. 2012, 16, 2014.
6. Z. Chen, H. Li, X. Zheng, Q. Zhang, Z. Li, Y. Hao, G. Fang, ChemSusChem 2017, 10, 3111.
7. X. X. Liu, X. Ding, Y. Ren, Y. Yang, Y. Ding, X. X. Liu, A. Alsaedi, T. Hayat, J. Yao, S. Dai, J. Mater. Chem. C 2018, 6, 12912.
8. W. Yu, Q. Yang, J. Zhang, D. Tu, X. Wang, X. Liu, G. Li, X. Guo, C. Li, ACS Appl. Mater. Interfaces 2019, 11, 30065.
9. M. S. Kang, S. Do Sung, I. T. Choi, H. Kim, M. Hong, J. Kim, W. I. Lee, H. K. Kim, ACS Appl. Mater. Interfaces 2015, 7, 22213.
10. C. Lu, I. T. Choi, J. Kim, H. K. Kim, J. Mater. Chem. A 2017, 5, 20263.
11. F. Wu, Y. Ji, C. Zhong, Y. Liu, L. Tan, L. Zhu, Chem. Commun. 2017, 53, 8719.
12. A. Magomedov, S. Paek, P. Gratia, E. Kasparavicius, M. Daskeviciene, E. Kamarauskas, A. Gruodis, V. Jankauskas, K. Kantminiene, K. T. Cho, K. Rakstys, T. Malinauskas, V. Getautis, M. K. Nazeeruddin, Adv. Funct. Mater. 2018, 28, 1704351.
13. K. Rakstys, S. Paek, A. Drevilkauskaite, H. Kanda, S. Daskeviciute, N. Shibayama, M. Daskeviciene, A. Gruodis, E. Kamarauskas, V. Jankauskas, V. Getautis, M. K. Nazeeruddin, ACS AppL. Mater. Interfaces 2020, 12, 19710.
14. F. Wu, Y. Shan, J. Qiao, C. Zhong, R. Wang, Q. Song, L. Zhu, ChemSusChem 2017, 10, 3833.
15. D. Li, J. Y. Shao, Y. Y. Li, Y. Y. Li, L. Y. Deng, Y. W. Zhong, Q. Meng, Chem. Commun. 2018, 54, 1651.
16. N. Tsutsumi, M. Yamamoto, Y. Nishijima, J. Polym. Sci. Part B Polym. Phys. 1987, 25, 2139.
17. T. Sasakawa, T. Ikeda, S. Tazuke, J. Appl. Phys. 1989, 65, 2750.
18. T. Ikeda, H. Mochizuki, Y. Hayashi, M. Sisido, T. Sasakawa, J. Appl. Phys. 1991, 70, 3689.

The invention claimed is:

1. A photovoltaic cell comprising a conducting support layer, a surface-increasing scaffold layer, a sensitizer layer, a hole transporting layer, and a counter electrode, wherein the hole transport layer comprises a cyclobutane-based hole transport compound;
   wherein the cyclobutane-based hole transport compound is selected from:
   1,2-bis[3,6-bis(4,4'-dimethoxy)diphenylamino-9H-carbazol-9-yl]cyclobutane,
   1,2-bis{3,6-bis[N-(9-ethylcarbazol-3-yl)-N-(4-methoxyfenil)amino]-9H-carbazol-9-yl}cyclobutane, and
   1,2-bis|3,6-bis{4-[N,N-bis(4-methoxyfenil)amino]fenil}-9H-carbazol-9-yl|cyclobutene.

2. The photovoltaic cell according to claim 1, wherein the cyclobutane-based hole transport compound is 1,2-bis[3,6-bis(4,4'-dimethoxy)diphenylamino-9H-carbazol-9-yl] cyclobutene.

3. The photovoltaic cell according to claim 1, wherein the cell is an organic photovoltaic cell, a photovoltaic solid-state cell, or a dye sensitized solar cell.

4. The photovoltaic cell according to claim 1, further comprising an organic-inorganic perovskite as sensitizer.

5. The photovoltaic cell according to claim 4, wherein the organic-inorganic perovskite is a perovskite-type structure of formula (II):

$$AMX_3 \quad (II),$$

wherein:
A represents an organic monovalent cation chosen from Li+, Na+, K+, Rb+, Cs+, ammonium, or amidinium ion, wherein one or more hydrogens of said ammonium or amidinium ions comprise one or more substituents selected from alkyl or acyl groups or halogens, wherein said ammonium ion is mono, di, tri [and tetra alkyl ammonium ion; and wherein, the substituent alkyl group or groups are independently selected from C1-C6;
M is a divalent metal cation selected from the group consisting of $Cu^{2+}$, $Ni^{2+}$, $Co^{2+}$, $Fe^{2+}$, $Mn^{2+}$, $Cr^{2+}$, $Pd^{2+}$, $Cd^{2+}$, $Ge^{2+}$, $Sn^{2+}$, $Pb^{2+}$, $Eu^{2+}$, or $Yb^{2+}$; and
X is a monovalent anion, independently selected from Cl—, Br—, I—, NCS—, CN—, and NCO—.

6. The photovoltaic cell according to claim 4, wherein the organic-inorganic perovskite is a mixed perovskite-type structure according to formula (III):

$$A^1_{1-y}A^2_y P_b X^1_{3-z} X^2_z \quad (III)$$

wherein:
$A^1$ and $A^2$ are organic monovalent cations independently chosen from Li+, Na+, K+, Rb+, Cs+, ammonium, or amidinium ion; wherein one or more hydrogens of said ammonium or amidinium ions comprise one or more substituents selected from alkyl or acyl groups or halogens; wherein said ammonium ion is mono, di, tri and tetra alkyl ammonium ion; wherein, the substituent alkyl group or groups are independently selected from C1-C6;
$X^1$ and $X^2$ are the same or different monovalent anions selected from Cl$^-$, Br$^-$, I$^-$, NCS$^-$, CN$^-$ and NCO$^-$;
y is in the interval between 0.1 and 0.9; and
z is in the interval between 0.2 and 2.

7. The photovoltaic cell of claim 5, wherein A is methyl ammonium ion or formamidium ion and X is Br$^-$ or I$^-$.

8. The photovoltaic cell of claim 6, wherein $A^1$ is methyl ammonium ion, $A^2$ is formamidium ion, $X^1$ is Br$^-$ and $X^2$ is I$^-$.

9. The photovoltaic cell of claim 1, wherein the surface-increasing scaffold layer comprises Si, $TiO_2$, $SnO_2$, $Fe_2O_3$, ZnO, $WO_3$, $Nb_2O_5$, CdS, ZnS, PbS, $Bi_2S_3$, CdSe, CdTe, $SrTiO_3$, GaP, InP, GaAs, $CuInS_2$, $CuInSe_2$, or combinations thereof.

10. The photovoltaic cell of claim 1, wherein the hole transporting layer further comprises one or more of Li-bis(trifluoromethanesulfonyl) imide, [tris(2-(1H-pyrazol-1-yl)-4-tert-butylpyridine)-cobalt (III), tris(bis trifluoromethylsulfonyl)imide), and 4-tertbutylpyridine.

11. The photovoltaic cell of claim 1, wherein the conducting support layer comprises a conducting material selected from indium doped tin oxide (ITO), fluorine doped tinoxide (FTO), ZnO—$Ga_2O_3$, ZnO—$Al_2O_3$, tin-oxide, antimony doped tin oxide (ATO), $SrGeO_3$ and zinc oxide.

12. The photovoltaic cell of claim 11, further comprising a transparent substrate whereon the conducting material is applied.

13. The photovoltaic cell of claim 1, wherein each layer is configured to have a planar structure.

14. The photovoltaic cell of claim 1, wherein the conductive support layer is next to the surface-increasing scaffold layer, the scaffold layer is between the conductive support layer and the sensitizer layer, the sensitizer layer is between the surface-increasing scaffold layer and the hole transporting layer, and the hole transport layer is between the sensitizer layer and the counter-electrode layer.

15. A photovoltaic device comprising two or more photovoltaic cells of claim 1, wherein the photovoltaic cells are electrically connected in series or in parallel.

16. The photovoltaic cell according to claim 1, wherein the cyclobutane-based hole transport compound is 1,2-bis{3,6-bis[N-(9-ethylcarbazol-3-yl)-N-(4-methoxyfenil)amino-9H-carbazol-9-yl}cyclobutane.

17. The photovoltaic cell according to claim 1, wherein the cyclobutane-based hole transport compound is 1,2-bis|3,6-bis{4-[N,N-bis(4-methoxyfenil)amino]fenil}-9H-carbazol-9-yl|cyclobutane.

* * * * *